US011545262B2

(12) United States Patent
Yasui et al.

(10) Patent No.: US 11,545,262 B2
(45) Date of Patent: Jan. 3, 2023

(54) MOBILE BODY AND MANAGEMENT SYSTEM

(71) Applicant: HONDA MOTOR CO., LTD., Tokyo (JP)

(72) Inventors: Yuji Yasui, Wako (JP); Hisao Asaumi, Wako (JP); Shion Tokunaga, Wako (JP); Masashi Yuki, Wako (JP); Yo Ito, Tokyo (JP); Hirotaka Uchitomi, Tokyo (JP)

(73) Assignee: HONDA MOTOR CO., LTD., Tokyo (JP)

( * ) Notice: Subject to any disclaimer, the term of this patent is extended or adjusted under 35 U.S.C. 154(b) by 437 days.

(21) Appl. No.: 16/621,279

(22) PCT Filed: Jun. 13, 2018

(86) PCT No.: PCT/JP2018/022498
§ 371 (c)(1),
(2) Date: Dec. 11, 2019

(87) PCT Pub. No.: WO2018/230584
PCT Pub. Date: Dec. 20, 2018

(65) Prior Publication Data
US 2020/0143940 A1 May 7, 2020

(30) Foreign Application Priority Data
Jun. 16, 2017 (JP) .................. 2017-118917

(51) Int. Cl.
*G16H 40/67* (2018.01)
*G16H 40/20* (2018.01)
(Continued)

(52) U.S. Cl.
CPC ............ *G16H 40/67* (2018.01); *B60W 40/08* (2013.01); *B60W 60/0016* (2020.02);
(Continued)

(58) Field of Classification Search
CPC ........ G16H 40/67; G16H 10/60; G16H 40/20; B60W 40/08; B60W 60/0016;
(Continued)

(56) References Cited

U.S. PATENT DOCUMENTS

2017/0193314 A1* 7/2017 Kim ...................... H04L 67/10
2017/0267256 A1* 9/2017 Minster ............... B60W 50/085
(Continued)

FOREIGN PATENT DOCUMENTS

JP 2002-176566 6/2002
JP 2002-224053 8/2002
(Continued)

OTHER PUBLICATIONS

International Search Report and Written Opinion for International Application Serial No. PCT/JP2018/022498 dated Sep. 18, 2018, 9 pages.

*Primary Examiner* — Mohamed Barakat
(74) *Attorney, Agent, or Firm* — Amin, Turocy & Watson, LLP

(57) ABSTRACT

An automated driving vehicle (200) includes a communication device (220), a biometric information acquirer (240), and an automated driving controller (250). The communication device (220) is configured to transmit biometric information acquired by the biometric information acquirer (240) to an external device and receives a response signal including attribute information for the transmitted biometric information. The automated driving controller (250) is configured to execute automated driving according to route information formed on the basis of the attribute information included in the received response signal.

12 Claims, 15 Drawing Sheets

(51) Int. Cl.
*G16H 10/60* (2018.01)
*B60W 60/00* (2020.01)
*B60W 40/08* (2012.01)
*G01C 21/34* (2006.01)
*G05D 1/00* (2006.01)
*G06V 40/50* (2022.01)
*A61B 3/11* (2006.01)
*A61B 5/01* (2006.01)
*A61B 5/021* (2006.01)
*A61B 5/024* (2006.01)
*A61B 5/08* (2006.01)
*A61B 5/145* (2006.01)
*A61B 7/00* (2006.01)
*A61B 5/318* (2021.01)
*A61B 5/389* (2021.01)

(52) U.S. Cl.
CPC ....... *G01C 21/3407* (2013.01); *G05D 1/0088* (2013.01); *G06V 40/50* (2022.01); *G16H 10/60* (2018.01); *G16H 40/20* (2018.01); *A61B 3/112* (2013.01); *A61B 5/01* (2013.01); *A61B 5/021* (2013.01); *A61B 5/024* (2013.01); *A61B 5/0816* (2013.01); *A61B 5/14532* (2013.01); *A61B 5/14542* (2013.01); *A61B 5/318* (2021.01); *A61B 5/389* (2021.01); *A61B 7/003* (2013.01); *B60W 2540/221* (2020.02); *G05D 2201/0213* (2013.01)

(58) Field of Classification Search
CPC .......... B60W 2540/221; G05D 1/0088; G05D 2201/0213; G06V 40/50; A61B 3/112; A61B 5/01; A61B 5/021; A61B 5/024; A61B 5/0816; A61B 5/14532; A61B 5/14542; A61B 5/318; A61B 5/389; A61B 7/003
See application file for complete search history.

(56) References Cited

U.S. PATENT DOCUMENTS

2018/0113460 A1* 4/2018 Koda ................... G05D 1/0088
2018/0259959 A1* 9/2018 Yamada ............... G05D 1/0282

FOREIGN PATENT DOCUMENTS

| JP | 2004-171394 | 6/2004 |
| JP | 2004-357843 | 12/2004 |
| JP | 2008-234009 | 10/2008 |
| JP | 2015-133050 | 7/2015 |

* cited by examiner

FIG. 4

| VEHICLE ID | H000001 |
|---|---|
| CURRENT POSITION | x x, OTA-KU, TOKYO |
| OCCUPANT AGE | 5 YEARS OLD |
| OCCUPANT SEX | MAN |
| GET-ON POSITION | CHILD SEAT |
| BIOMETRIC INFORMATION — PULSE RATE | 118 |
| PULSE RATE | 117 |
| PULSE RATE | 121 |
| HEART RATE | 120 |
| BODY TEMPERATURE | 37.2 |
| BLOOD GLUCOSE LEVEL | 91 |
| BLOOD OXYGEN CONCENTRATION | 99 |

FIG. 11

| HOSPITAL NAME | ADDRESS | MEDICAL SUBJECT | NON-CONSULTATION DAY |
|---|---|---|---|
| HOSPITAL A | ××, OTA-KU, TOKYO | PEDIATRICS AND INTERNAL MEDICINE | SUNDAY |
| HOSPITAL B | ××, SETAGAYA-KU, TOKYO | PEDIATRICS | SATURDAY AND SUNDAY |
| HOSPITAL C | ××, CHIYODA-KU, TOKYO | PEDIATRICS AND INTERNAL MEDICINE | THURSDAY (AFTERNOON), SATURDAY, AND SUNDAY |

⋮

MOBILE BODY AND MANAGEMENT SYSTEM

TECHNICAL FIELD

The present invention relates to a mobile body and a management system.

Priority is claimed on Japanese Patent Application No. 2017-118917, filed Jun. 16, 2017, the content of which is incorporated herein by reference.

BACKGROUND ART

In the related art, there is a health management assistance system that notifies an occupant of a vehicle of advice on the basis of physical information and an activity situation of the occupant as a system that manages the health of the occupant of the vehicle (see, for example, Patent Document 1). In this health management assistance system, it is possible to manage the health of the occupant by detecting physical information of the occupant and advising the occupant.

CITATION LIST

Patent Document

[Patent Document 1]
Japanese Unexamined Patent Application, First Publication No. 2008-234009

SUMMARY OF INVENTION

Technical Problem

However, in the health management assistance system disclosed in Patent Document 1 described above, when one person is in a vehicle, it is necessary to stop the vehicle and acquire physical information. On the other hand, when a configuration in which physical information can be acquired even while driving is adopted, types of physical information are limited, and thus, sufficient information to ascertain the health of the occupant cannot be acquired in some cases.

An object of the present invention is to provide a mobile body and a management system capable of contributing to acquiring and transferring a physical status of a user quickly and sufficiently.

Solution to Problem (1) A mobile body including: a biometric information acquirer configured to acquire biometric information of a user; an automated driving controller configured to execute automated driving of the mobile body; and a communicator configured to transmit the biometric information to an external device and receive a response signal including attribute information for the transmitted biometric information from the external device, wherein the automated driving controller is configured to execute the automated driving according to route information formed on the basis of the attribute information included in the response signal.

(2) In the mobile body according to (1), the attribute information includes position information according to at least one of diagnosis result information and additional diagnosis necessity information of the user, and the automated driving controller is configured to select a waypoint from the position information included in the attribute information received by the communicator.

(3) The mobile body according to (2) includes a continuous connection provider configured to continuously transmit the biometric information acquired by the biometric information acquirer to the external device through mutual authentication with the external device.

(4) The mobile body according to (2) includes a guider configured to generate guidance information for guiding another mobile body to a route of the mobile body on the basis of the attribute information and the route information, and the communicator is configured to transmit the guidance information to an outside.

(5) In the mobile body according to any one of (1) to (4), the automated driving controller is configured to cause the mobile body to stop or slow down while the biometric information acquirer is in operation.

(6) The mobile body according to any one of (1) to (5) includes an attribute display controller configured to control information to be displayed to the user on the basis of the attribute information.

(7) The mobile body according to any one of (1) to (6) includes a primary attribute determiner configured to determine a primary attribute regardless of the communicator.

(8) A management system communicatively connectable to a mobile body including a biometric information acquirer configured to acquire biometric information of a user, an automated driving controller configured to execute automated driving of the mobile body, and a communicator configured to transmit the biometric information to an external device and receive a response signal including attribute information for the transmitted biometric information from the external device, the management system including: a response generator configured to add an attributes to the biometric information on the basis of the biometric information received from the communicator and generate the response signal including the attribute information; a user information acquirer configured to acquire user information associated with the biometric information; and a transmitter configured to transmit the response signal to the communicator.

(9) The management system according to (8) includes a facility information referrer configured to refer to facility information of an available facility on the basis of the attribute information.

(10) The management system according to (9) includes: an inquiry signal transmitter configured to transmit an inquiry signal to a communication destination associated with the available facility on the basis of the attribute information; and a facility information transmitter configured to receive an inquiry response in response to the inquiry signal from the communication destination and transmit the facility information associated with the inquiry response to the communicator.

(11) The management system according to (8) includes: a continuous reception determiner configured to determine whether or not the biometric information is able to be continuously received from the communicator; a signal converter configured to convert the received biometric information and write the converted biometric information to a unit sharable with an external device in a state in which the continuous reception determiner has determined that the biometric information is able to be continuously received; and a connection permitter configured to permit an external device to access the shareable unit.

(12) The management system according to (10) includes: a signal holder configured to record the biometric information from the communicator over a predetermined period;

and a history transmitter configured to transmit a biometric signal history recorded by the signal holder to the communication destination.

In (1) and (8), the mobile body is configured to transmit the biometric information to the external device and is configured to execute automated driving according to route information based on the attribute information received from the external device. Therefore, by a doctor or the like operating the external device, the mobile body can determine the necessity of a treatment to be taken by the user, such as a hospital visit treatment or a medicine administration treatment on the basis of the biometric information of the user, and move according to the biometric information of the user. Therefore, it is possible to acquire and transfer a physical status of the user quickly and sufficiently.

In (2), the automated driving controller is configured to select a waypoint from position information according to at least one of the diagnosis result information and the additional diagnosis necessity information of the user. Therefore, the user can move via an appropriate facility.

In (3) and (11), the biometric information acquired by the biometric information acquirer is continuously transmitted to the external device through mutual authentication with the external device. Therefore, the biometric information of the user and a health condition can be recognized at any time.

In (4), guidance information for guiding another mobile body on the route is generated on the basis of the attribute information and the route information. Therefore, for example, when the user has a condition with a high urgency level, it is possible to cause another mobile body such as a medical vehicle to be dispatched early.

In (5), the automated driving controller is configured to cause the mobile body to stop or slow down while the biometric information acquirer is in operation. Therefore, it is possible to acquire the biometric information of the user accurately.

In (6), information to be displayed to the user is controlled on the basis of the attribute information. Therefore, the attribute information according to the user can be displayed.

In (7), a primary attribute determiner that determines a primary attribute is included. Therefore, a temporary attribute of the user can be determined inside the mobile body.

In (9), a facility information referrer that refers to facility information of an available facility on the basis of the attribute information of the user is included. Therefore, a facility according to the user can be selected.

In (10), the facility information associated with the inquiry response is transmitted to the communicator of the mobile body. Therefore, the facility according to the user can be provided to the mobile body such as the automated driving vehicle.

In (12), the biometric signal history recorded by the signal holder is transmitted to the communication destination. Therefore, the facility according to the user can be provided to the mobile body such as the automated driving vehicle.

BRIEF DESCRIPTION OF DRAWINGS

FIG. 4 is an illustrative diagram showing transmission data.

FIG. 11 is an illustrative diagram showing data of a hospital that is a destination candidate.

DESCRIPTION OF EMBODIMENTS

Hereinafter, a medical network system of the present invention will be described with reference to the drawings. The medical network system is a system for assisting in a treatment when a user getting on an automated driving vehicle has experienced poor physical condition. In the medical network system, biometric information of the user is acquired, and the acquired biometric information is provided to a remote diagnostician or the like. The remote diagnostician determines a physical condition of the user on the basis of the provided biometric information of the user.

When the remote diagnostician has determined that the user is to visit a hospital, the remote diagnostician provides information for allowing the user to visit the hospital to the user. Further, the remote diagnostician provides biometric information of the user to the hospital that the user visits. Thus, it is possible for a user needing to have a medical examination while being on the automated driving vehicle to have the medical examination early, and to take an appropriate treatment even while being on the automated driving vehicle.

Further, when a visit to a hospital is not necessary, but medicine administration according to a physical condition is effective, information on appropriate medicines is provided to the user. Accordingly, when a doctor's diagnosis is not necessary and the physical condition is a physical condition in which the administration of medicine suffices, it is possible to omit the visit to the hospital. Further, information on medicine to be administered can be provided to the user. Hereinafter, a first embodiment of the medical network system will be described. A user in the medical network system is an occupant getting on the automated driving vehicle, and may be a driver or may be a person (a fellow occupant) other than the driver.

First Embodiment

Figure 1:
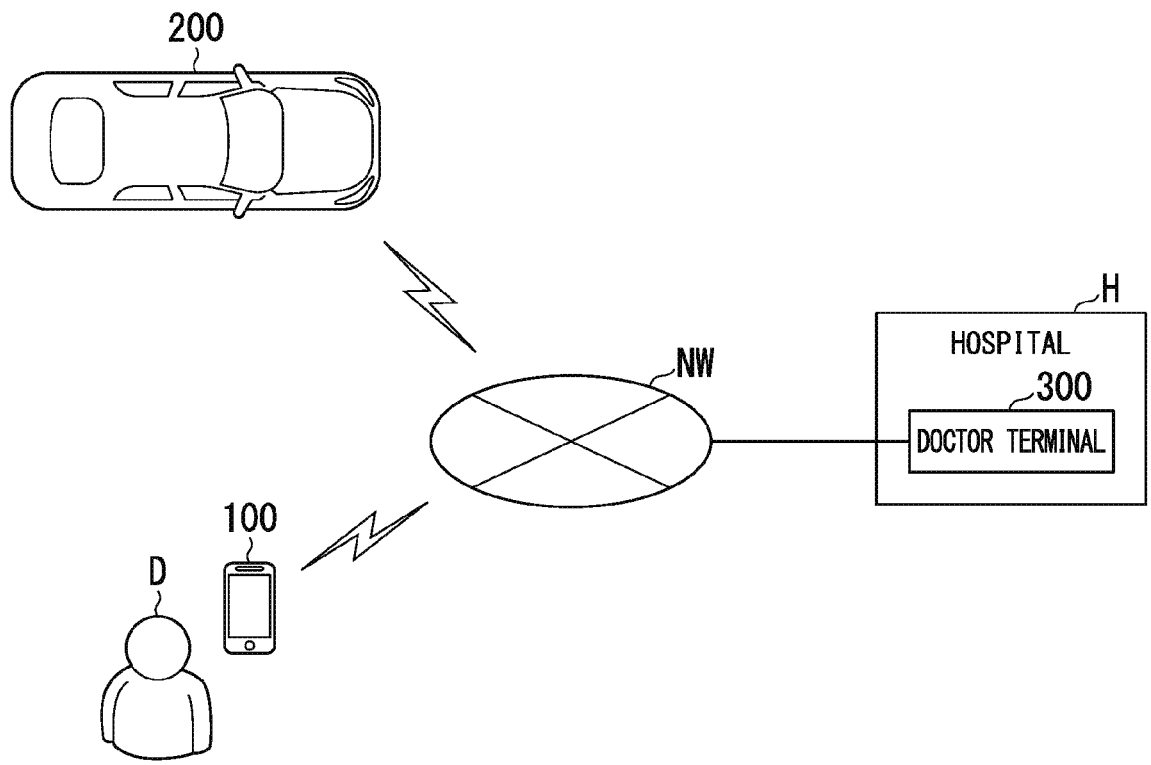
FIG. 1 is a configuration diagram of a medical network system according to a first embodiment.

FIG. 1 is a configuration diagram of a medical network system according to a first embodiment. As shown in FIG. 1, the medical network system includes, for example, an external terminal 100, an automated driving vehicle 200, and a doctor terminal 300. The external terminal 100 is used by a remote diagnostician D, for example. The doctor terminal 300 is installed in a hospital H that is a medical institution, for example. In the first embodiment, the hospital H shown in FIG. 1, which is a medical institution that the automated driving vehicle 200 visits, is determined by the remote diagnostician D.

The external terminal 100 and the automated driving vehicle 200 can be connected to a network NW through wireless communication. Further, the doctor terminal 300 is connected to the network NW via a cable. The network NW includes the Internet, a wide area network (WAN), a local area network (LAN), a public line, a provider device, a dedicated line, a wireless base station, and the like.

The external terminal 100 is, for example, a smartphone, a tablet terminal, or a personal computer. In the external terminal 100, an application program, a browser, or the like for use of the medical network system is activated to support services to be described below. In the following description, it is assumed that the external terminal 100 is a smartphone and an application program (a medical network application) is activated.

Figure 2:
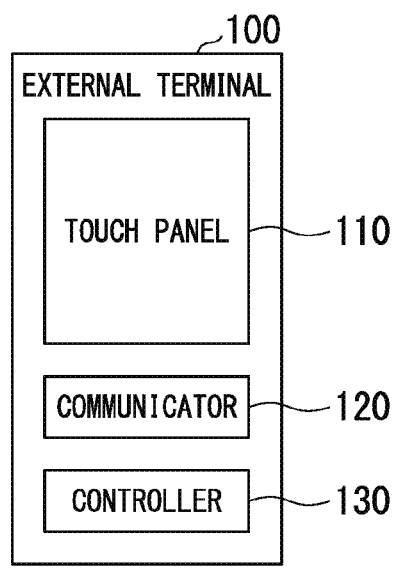
FIG. 2 is a configuration diagram of an external terminal.

FIG. 2 is a configuration diagram of an external terminal device. As shown in FIG. 2, the external terminal 100 includes a touch panel (an example of an input and an output) 110, a communicator (an example of a second communicator) 120, and a controller 130. The touch panel 110 receives an input operation of the remote diagnostician D who is a user. Examples of content of the input operation include an instruction to transmit the biometric information to the doctor terminal 300 of the hospital H, and an instruction to transmit hospital visit necessity information including information such as a designation of the hospital H and identification information or location of the designated hospital to a biometric information processor 242 of the automated driving vehicle 200. The touch panel 110 outputs input information according to the input operation to the controller 130. Further, the touch panel 110 displays and outputs information received by the communicator 120, such as information based on biometric information that is transmitted by the communication device 220 of the automated driving vehicle 200.

The communicator 120 is, for example, a wireless communication module for connection to the network NW or a wireless communication module with the automated driving vehicle 200 and the doctor terminal 300 via the network NW. The communicator 120 performs wireless communication on the basis of Wi-Fi, dedicated short range communications (DSRC), Bluetooth (registered trademark), and other communication standards. The communicator 120 outputs information transmitted by the automated driving vehicle 200 to the controller 130.

The controller 130 is realized by, for example, a processor such as a central processing unit (CPU) executing programs stored in various storage devices. The controller 130 performs various calculation processes on the basis of information input from the touch panel 110. The controller 130 outputs information based on results of various calculation processes to the touch panel 110 and the communicator 120. The communicator 120 transmits the information output by the controller 130 to the automated driving vehicle 200 or the doctor terminal 300 via the network NW.

Further, the external terminal 100 may include a speaker or a vibrator (not shown). The external terminal 100 can output a sound via a speaker. The sound here may indicate, for example, that predetermined information has been received or a type of information when the predetermined information is received, or may be a predetermined mechanical sound according to the received information. Further, the vibrator notifies the user of the external terminal 100 that the information has been received through vibration. The external terminal 100 having these configurations executes external terminal processing. The external terminal processing will be described below.

Figure 3:
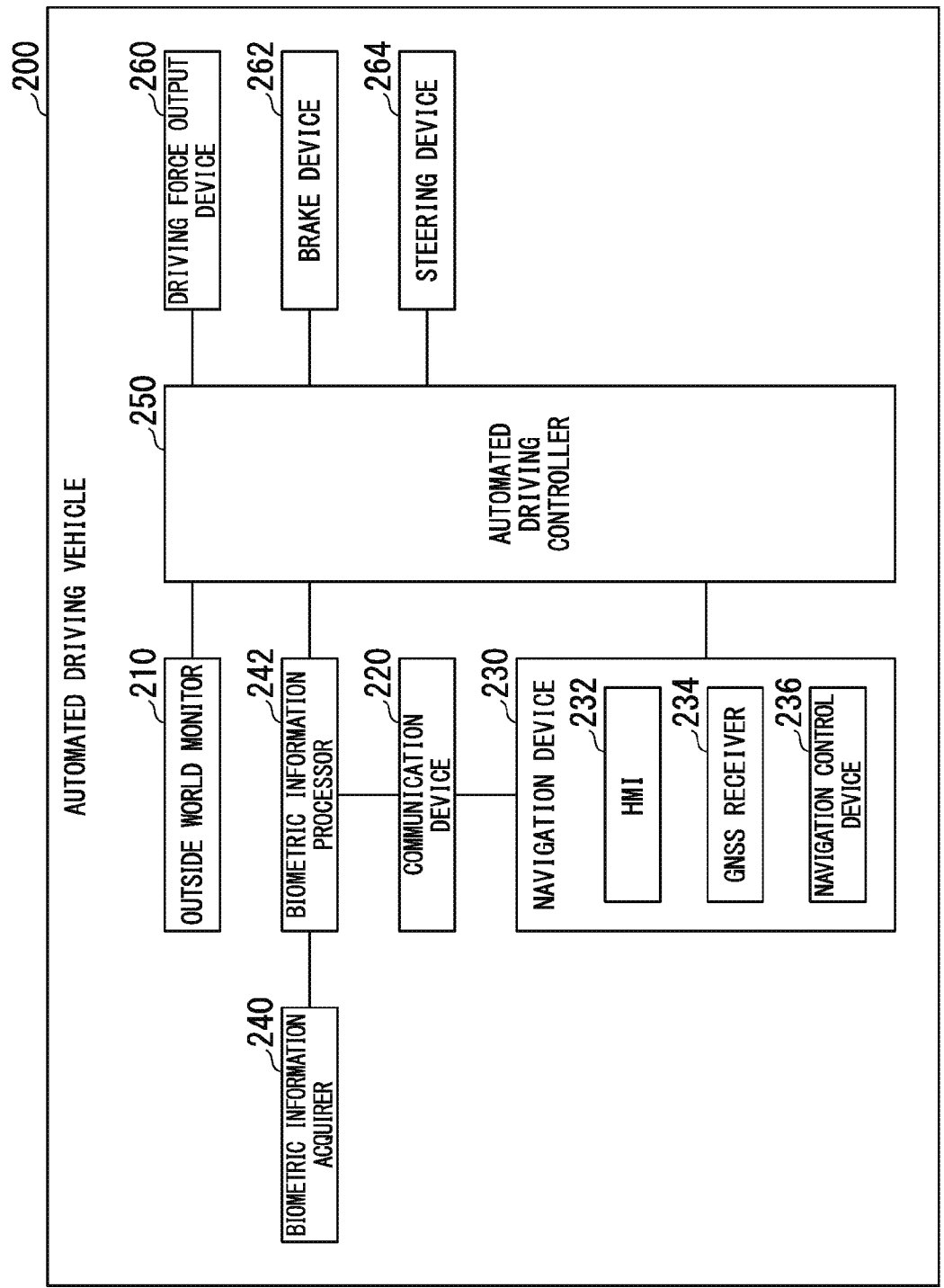
FIG. 3 is a configuration diagram of an automated driving vehicle.

The automated driving vehicle 200 is, for example, a vehicle on which one or more users can get as occupants and is a vehicle having a function of allowing the user to travel without performing a driving operation. FIG. 3 is a configuration diagram of the automated driving vehicle 200. As shown in FIG. 3, the automated driving vehicle 200 includes, for example, an outside world monitor 210, a communication device (an example of a first communicator) 220, a navigation device 230, a biometric information acquirer 240, the biometric information processor 242, an automated driving controller (an example of an automated driving controller) 250, a driving force output device 260, a brake device 262, and a steering device 264.

The outside world monitor 210 includes, for example, a camera, a radar, a light detection and ranging (LIDAR), and an object recognition device that performs sensor fusion processing on the basis of outputs thereof. The outside world monitor 210 estimates types of objects (particularly, vehicles, pedestrians, and bicycles) present around the automated driving vehicle 200, and outputs the types to an automated driving controller 250 together with information on positions or speeds.

The communication device 220 is, for example, a wireless communication module for connection to the network NW or direct communication with a terminal device of another vehicle or a pedestrian. The communication device 220 performs wireless communication on the basis of Wi-Fi, dedicated short range communications (DSRC), Bluetooth (registered trademark), or other communication standards. As the communication device 220, a plurality of communication devices may be prepared according to applications. The communication device 220 outputs information transmitted by the external terminal 100 to the biometric information processor 242. The communication device 220 transmits information output by the navigation device 230 and the biometric information processor 242 to the external terminal 100 and the doctor terminal 300 via the network NW.

The navigation device 230 includes, for example, a human machine interface (HMI) 232, a global navigation satellite system (GNSS) receiver 234, and a navigation control device 236. The HMI 232 includes, for example, a touch panel display device, a speaker, and a microphone. The GNSS receiver 234 measures a position of the own device (a position of the automated driving vehicle 200) on the basis of radio waves coming from a GNSS satellite (for example, a GPS satellite). The navigation control device 236 includes, for example, a central processing unit (CPU) and various storage devices, and controls the entire navigation device 230.

Map information (navigation map) is stored in the storage device. The navigation map is a map representing roads using nodes and links. The navigation control device 236 determines a route from the position of the automated driving vehicle 200 measured by the GNSS receiver 234 to the destination designated using the HMI 232, by referring to the navigation map. Further, the navigation control device 236 may transmit the position and the destination of the automated driving vehicle 200 to a navigation server (not shown) using the communication device 220 and acquire a route replied from the navigation server. The route may include information on a point at which the automated driving vehicle 200 stops to cause the user to get on or off, and a target arrival time. The navigation control device 236 outputs route information of the route determined by any one of the above methods to the communication device 220 and the automated driving controller 250.

The biometric information acquirer 240 acquires the biometric information of the user. For example, the biometric information acquirer 240 is a camera that is mounted in the automated driving vehicle and images the user, a microphone, or a wearable sensor worn by the user. Examples of biometric information of the user that the biometric information acquirer 240 operates and acquires include a heart rate, a pulse rate, a body temperature, a respiratory rate, a degree of pupil opening, a respiratory sound, an electrocardiogram, an electromyogram, a change (displacement) in the electrocardiogram or the electromyogram, a blood glucose level, and a blood oxygen concentration. For measurement of these items, for example, a dedicated measurement device for each item such as an electrocardiograph, an electromyograph, a blood glucose level meter, and a blood oxygen concentration measurement instrument may be used.

The biometric information processor 242 is realized by one or more processors such as a CPU or a micro processing unit (MPU) executing programs stored in various storage devices. The biometric information processor 242 outputs a biometric information detection instruction to the biometric information acquirer 240. The biometric information acquirer 240 detects the biometric information of the user according to the biometric information detection instruction output by the biometric information processor 242. Further, the biometric information processor 242 outputs a deceleration instruction to the automated driving controller 250 when the biometric information processor 242 outputs the biometric information detection instruction to the biometric information acquirer 240.

The biometric information processor 242 outputs the biometric information output by the biometric information acquirer 240 to the communication device 220. The communication device 220 transmits the output biometric information to the external terminal 100 via the network NW. A specific procedure of biometric information processing will be further described below. The external terminal 100 receives the transmitted biometric information. Further, the biometric information processor 242 sets a destination according to the information transmitted by the external terminal 100, and outputs destination information according to the set destination to the navigation device 230.

The automated driving controller 250 includes one or more processors such as a CPU or an MPU and various storage devices. The automated driving controller 250 executes automated driving for causing the automated driving vehicle 200 to automatically travel so that the automated driving vehicle 200 travels along a route based on the route information transmitted by the navigation device 230. The automated driving controller 250, for example, sequentially executes various events. Examples of the events include a constant-speed traveling event in which a vehicle travels on the same traveling lane at a constant speed, a following event in which a vehicle follows a preceding vehicle, a lane changing event, a merging event, a branching event, an emergency stopping event, a toll gate event for passing through a toll gate, and a handover event for ending automated driving and switching to manual driving. Further, an action for avoidance may also be planned on the basis of a situation of surroundings of the automated driving vehicle 200 (presence of nearby vehicles or pedestrians, lane narrowing due to road construction, or the like) during execution of these events.

The automated driving controller 250 generates a target trajectory on which the automated driving vehicle 200 will travel in the future. The target trajectory includes, for example, a velocity element. For example, the target trajectory is represented as a sequence of points (trajectory points) that the automated driving vehicle 200 will reach. The trajectory points are points that the automated driving vehicle 200 will reach at each of predetermined travel distances. Separately, a target speed and a target acceleration at each predetermined sampling time (for example, every several tenths of a [sec]) are generated as a part of the target trajectory. Further, the trajectory points may be positions that a host vehicle M will reach at a predetermined sampling time for each of predetermined sampling times. In this case, information on the target speed or the target acceleration is represented using an interval between the trajectory points.

When the deceleration instruction is output by the biometric information processor 242, the automated driving controller 250 determines whether or not deceleration is difficult, and performs a deceleration process when the deceleration is not difficult, for example, there is no following vehicle at a close distance. Thus, the automated driving controller 250 performs the deceleration process to cause the automated driving vehicle 200 to stop or slow down while the biometric information acquirer 240 is in operation. When the biometric information acquirer 240 is likely to be influenced by radio noise (electromagnetic waves) in a surrounding environment, the automated driving vehicle 200 may move to another place to avoid the influence of the radio noise, and then, the biometric information acquirer 240 may acquire the biometric information. Therefore, for example, an S/N ratio is detected, and when the S/N ratio is low, the automated driving vehicle 200 may be moved to a position in which the S/N ratio is high.

The driving force output device 260 outputs a travel driving force (torque) for travel of the vehicle to driving wheels. The driving force output device 260 includes, for example, a combination of an internal combustion engine, an electric motor, a transmission, and the like, and a power ECU that controls these. The power ECU controls the above configuration according to information input from the automated driving controller 250 or information input from a driving operator (not shown).

The brake device 262 includes, for example, a brake caliper, a cylinder that transfers hydraulic pressure to the brake caliper, an electric motor that generates the hydraulic pressure in the cylinder, and a brake ECU. The brake ECU controls the electric motor according to information input from the automated driving controller 250 or information input from the driving operator so that a brake torque according to a braking operation is output to each wheel. The brake device 262 may include a mechanism that transfers the hydraulic pressure generated by an operation of a brake pedal included in the driving operator to the cylinder via a master cylinder, as a backup. The brake device 262 is not limited to the configuration described above, but may be an electronically controlled hydraulic brake device that controls an actuator according to the information input from the automated driving controller 250 and transfers the hydraulic pressure of the master cylinder to the cylinder.

The steering device 264 includes, for example, a steering ECU and an electric motor. The electric motor, for example, applies a force to a rack and pinion mechanism to change directions of steerable wheels. The steering ECU drives the electric motor according to the information input from the automated driving controller 250 or the information input from the driving operator to change the directions of the steerable wheels.

Referring back to FIG. 1, the doctor terminal 300 includes, for example, a communication device, a calculation device, and an image display device (not shown). The doctor terminal 300 can receive transmission information including the biometric information transmitted by the external terminal 100 via the network NW using the communication device. Further, the doctor terminal 300 can display the received biometric information on the image display device. A doctor in the hospital H who operates the doctor terminal 300 can prepare for a secondary diagnosis for more accurately diagnosing the user on the basis of the biometric information transmitted by the external terminal 100.

The external terminal 100 generates, for example, transmission information including the biometric information (or information obtained by processing the biometric information) on the basis of the biometric information transmitted by the communication device 220 in the automated driving vehicle 200. The transmission information includes items of "vehicle ID", "current position (of the automated driving vehicle 200)", "occupant age", "occupant sex", "get-on position", "pulse rate", "heart rate", and "body temperature", for example, as shown in FIG. 4. Among these items, "pulse rate", "heart rate", "body temperature", "blood glucose level", and "blood oxygen concentration" are biometric information. The biometric information acquirer 240, for example, acquires the biometric information of the user in a time series. For the biometric information, for example, the biometric information of the user is acquired in a time series at a frequency of about 120 Hz or less. The transmission information shown in FIG. 4 indicates transmission information including the biometric information measured at times t1, t2, t3, t4, and t5. The external terminal 100 transmits the generated transmission information to the doctor terminal 300 via the network NW.

Next, a processing in the medical network system of the first embodiment will be described. The processing in the medical network system includes biometric information processing that is executed by the biometric information processor 242 and external terminal processing that executed by the external terminal 100. The biometric information processing and the external terminal processing are performed, for example, in a state in which an occupant has got on the automated driving vehicle 200 and the automated driving vehicle 200 is traveling toward a set destination. Hereinafter, the biometric information processing and the external terminal processing will be specifically described.

Figure 5:
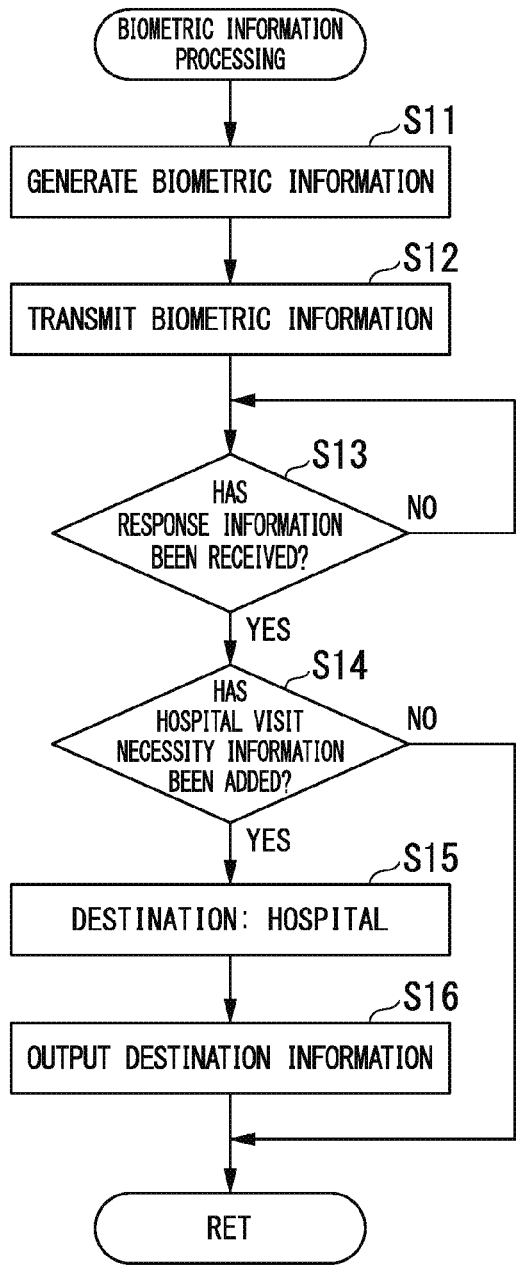
FIG. 5 is a flowchart showing a procedure of biometric information processing according to the first embodiment.

FIG. 5 is a flowchart showing an example of a procedure of the biometric information processing. First, the biometric information processor 242 causes the biometric information acquirer 240 to acquire the biometric information of the occupant (step S11). The biometric information processor 242, for example, causes the biometric information acquirer 240 to acquire the biometric information of the occupant and output the biometric information to the biometric information processor 242 at regular intervals. The biometric information acquirer 240, for example, may compress and transmit data of several seconds to tens of seconds obtained by measuring the biometric information in a time series. When the biometric information acquirer 240 compresses and transmits the data, the biometric information acquirer 240 may compress and transmit, for example, a plurality of pieces of transmission information shown in FIG. 4.

Then, the biometric information processor 242 transmits the biometric information output by the biometric information acquirer 240 to the external terminal 100 via the communication device 220 (step S12). Then, the biometric information processor 242 determines whether or not response information transmitted by the external terminal 100 has been received (step S13). As a result, when the biometric information processor 242 has determined that the response information has not been received, the biometric information processor 242 repeats a process of step S13 until the biometric information processor 242 receives the response information. In a case in which the biometric information processor 242 does not receive the response information even when a predetermined waiting time such as 15 minutes has elapsed, the biometric information processor 242 may determine timeout as it is and end the biometric information processing.

The external terminal 100 performs processing based on the biometric information transmitted by the biometric information processor 242 of the automated driving vehicle 200, and transmits response information as a result of the processing to the biometric information processor 242. Therefore, the external terminal processing that is executed by the controller 130 in the external terminal 100 will be described prior to continuing the description of the biometric information processing in the biometric information processor 242.

Figure 6:
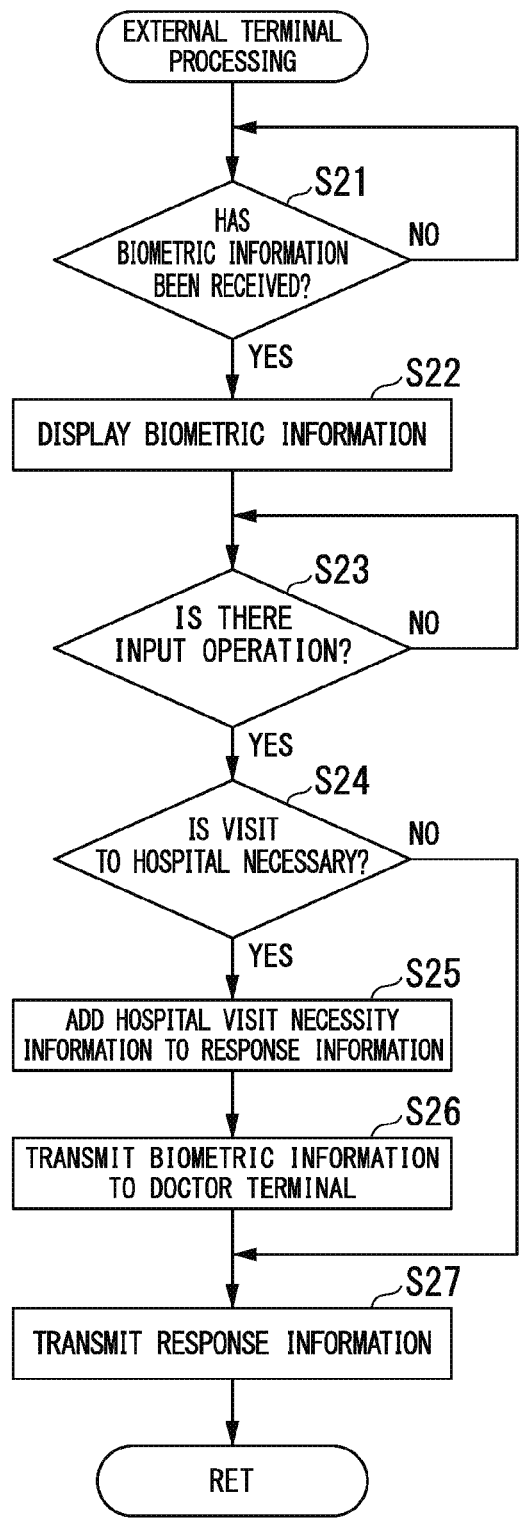
FIG. 6 is a flowchart showing a procedure of external terminal processing according to the first embodiment.

FIG. 6 is a flowchart showing an example of a procedure of the external terminal processing. First, the controller 130 in the external terminal 100 determines whether or not the biometric information transmitted by the biometric information processor 242 of the automated driving vehicle 200 has been received (step S21). As a result, when the controller 130 has determined that the controller 130 has not received the biometric information, the controller 130 repeats a process of step S21 until the controller 130 receives the biometric information.

When the controller 130 has determined in step S21 that the controller 130 has received the biometric information, the controller 130 causes an image based on the received biometric information to be displayed on the touch panel 110 (step S22). In this case, the controller 130 may cause a display sound to be output by the speaker of the external terminal 100 or cause the vibrator to vibrate, thereby notifying the user of the external terminal 100 that the image based on the biometric information has been displayed on the touch panel 110.

The remote diagnostician D performs a primary diagnosis of the occupant on the basis of the image displayed on the external terminal 100. For example, when a pulse rate or heart rate is higher than a normal value or when a body temperature is higher than a normal temperature, the remote diagnostician D performs a primary diagnosis such as there being a suspicion of disease and a visit to the hospital H being necessary. The remote diagnostician D who has performed the diagnosis operates the touch panel 110 to input a diagnosis result.

Subsequently, the controller 130 determines whether or not the remote diagnostician D has performed an operation for inputting the diagnosis result with respect to the touch panel 110 (step S23). As a result, when the controller 130 has determined that the touch panel 110 has not been operated, the controller 130 repeats the process of step S23 until the touch panel 110 is operated. Further, when the controller 130 has determined that the touch panel 110 has been operated, the process proceeds to step S24. The remote diagnostician D inputs the necessity of a visit to the hospital, and identification information or a location of the hospital to be visited using the touch panel 110. The identification information or the like of the hospital may be determined on the basis of, for example, experience of the remote diagnostician D, or a separate hospital list may be prepared and the remote diagnostician D may select and determine the identification information or the like from this hospital list. When there is no input operation even when a predetermined waiting time such as 10 minutes has elapsed, the controller 130 may determine timeout as it is and end the external terminal processing.

The primary diagnosis based on the biometric information may be performed by the remote diagnostician D or may be performed by other specialists such as nurses or consultants. Further, the diagnosis may be performed by a plurality of persons including doctors including the remote diagnostician D or other specialists, or the controller 130 may perform the diagnosis using a diagnosis program or the like. When the controller 130 automatically performs a diagnosis, an input operation with respect to the touch panel 110 may be omitted.

Subsequently, the controller 130 determines whether or not a visit to the hospital H is necessary (whether or not the remote diagnostician D has input that the visit to the hospital H is necessary), by referring to the input diagnosis result (step S24). As a result, when the controller 130 has determined that the visit to the hospital H is necessary, the controller 130 adds hospital visit necessity information indicating that the visit to the hospital H is necessary to the response information (step S25). Then, the controller 130 transmits the information including the biometric information to the doctor terminal 300 (step S26). The controller 130 transmits the response information to the biometric information processor 242 of the automated driving vehicle 200 (step S27) and ends the external terminal processing. Further, when the controller 130 has determined that the visit to the hospital H is not necessary, the controller 130 transmits the response information to the biometric information processor 242 of the automated driving vehicle 200 without adding the hospital visit necessity information to the response information and without transmitting the biometric information to the doctor terminal 300 (step S27). Thus, the controller 130 ends the external terminal processing.

Return to the biometric information processing shown in FIG. 5. When the biometric information processor 242 has determined in step S13 that the biometric information processor 242 has received the response information, the biometric information processor 242 determines whether or not the hospital visit necessity information has been added (step S14). As a result, when the biometric information processor 242 has determined that the hospital visit necessity information has been added, the biometric information processor 242 sets the destination to the hospital H (step S15). Subsequently, the biometric information processor 242 outputs set destination information to the navigation device 230 (step S16). In the navigation device 230, the destination is changed from a preset destination to the hospital H. The navigation device 230 may notify the occupant that the destination has been changed through audio or image display. Further, in step S14, when the biometric information processor 242 has determined that the hospital visit necessity information has not been added, the biometric information processor 242 keeps the destination as it is without changing the destination. Thus, the biometric information processor 242 ends the biometric information processing.

Thus, in the medical network system according to the first embodiment, the biometric information of the user acquired by the biometric information acquirer 240 is transmitted to the external terminal 100 carried by the remote diagnostician D. Therefore, since the primary diagnosis can be performed on the basis of the biometric information by the remote diagnostician D carrying the external terminal 100, it is possible to acquire and transfer a physical status of the user quickly and sufficiently.

Therefore, the user can determine the necessity of an appropriate process to be taken by himself or herself, such as a hospital visit treatment or a medicine administration treatment, and provide a result of the determination to the automated driving vehicle. Thus, the user can take an appropriate treatment, such as visiting the hospital H even when the user is in the automated driving vehicle 200, early by following the determination of the remote diagnostician D.

Further, in the medical network system of the first embodiment, the destination of the automated driving vehicle 200 is determined on the basis of the identification information or the location of the hospital that the remote diagnostician D has input to the touch panel 110 of the external terminal 100. Therefore, since the hospital that is a destination can be determined on the basis of information input by a specialist such as the remote diagnostician D, an appropriate hospital can be set when a user is directed to a destination.

Further, in the medical network system of the first embodiment, the external terminal 100 transmits the biometric information, which has been transmitted by the biometric information processor 242, to the doctor terminal 300 of the hospital H. Therefore, in the hospital H, it is possible to proceed with preparations for accepting the user by referring to the biometric information. Thus, it is possible for a user needing to have a medical examination while being on the automated driving vehicle to receive the medical examination early.

Further, in the medical network system according to the first embodiment, the automated driving controller 250 in the automated driving vehicle 200 may cause the automated driving vehicle to stop or decelerate when the biometric information acquirer 240 is operating to acquire the biometric information of the user. Therefore, it is possible to reduce a vibration due to traveling of the automated driving vehicle 200 during the acquisition of the biometric information of the user in the biometric information acquirer 240. Therefore, it is possible to enhance detection accuracy in the biometric information acquirer 240. Further, when the biometric information processor 242 is likely to be influenced by radio noise in a surrounding environment, the automated driving vehicle 200 moves to another place such that the biometric information processor 242 can reliably acquire the biometric information.

Second Embodiment

Figure 7:
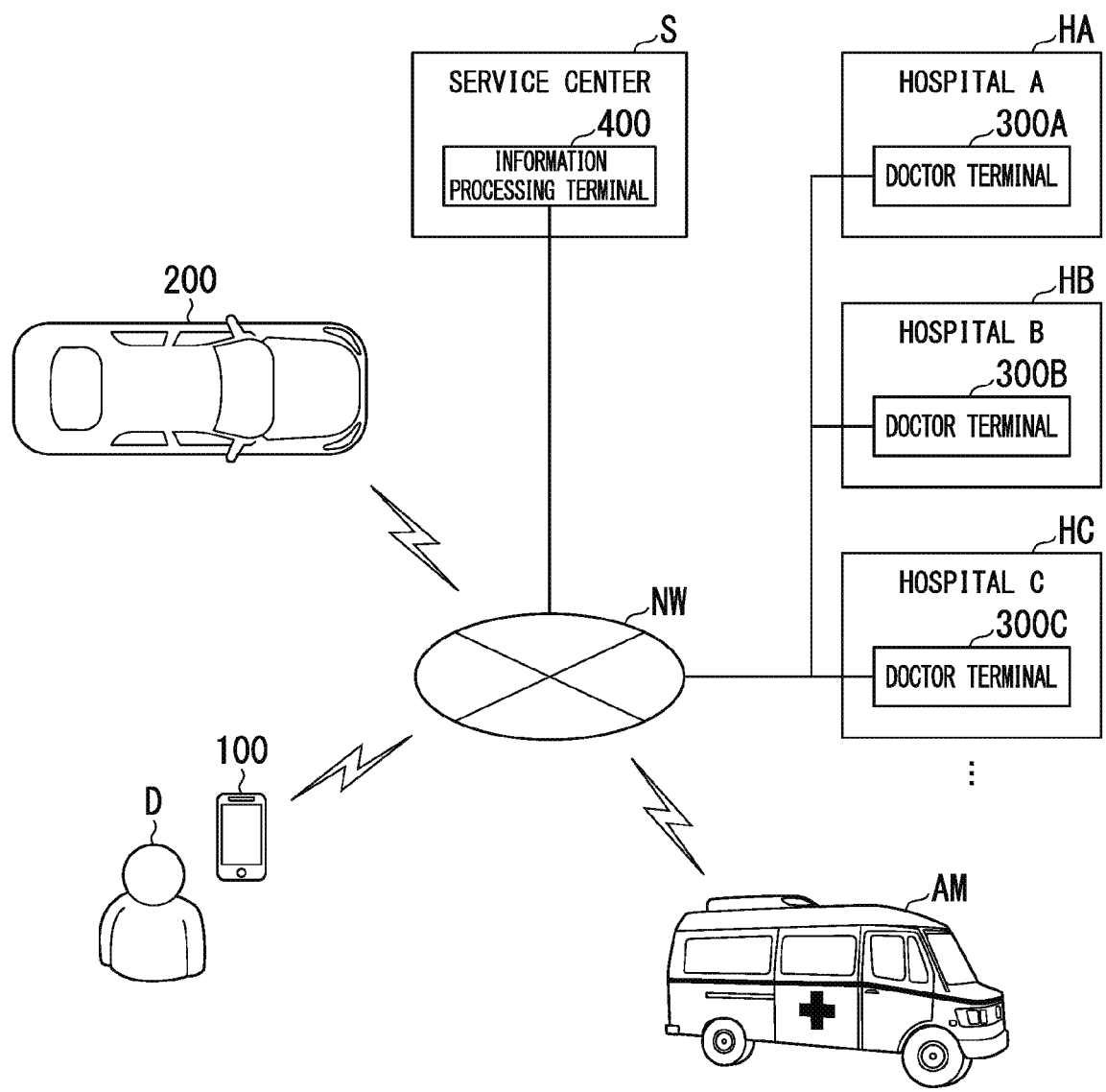
FIG. 7 is a configuration diagram of a medical network system of a second embodiment.

Next, a second embodiment will be described. In the second embodiment, a medical institution selected from among a plurality of medical institutions is designated as a medical institution that an automated driving vehicle visits, unlike the first embodiment. FIG. 7 is a configuration diagram of a medical network system of the second embodiment. As shown in FIG. 7, the medical network system of the second embodiment includes an external terminal 100 and an automated driving vehicle 200, as in the first embodiment. Further, the medical network system of the second embodiment includes a plurality of doctor terminal 300A, 300B, 300C, . . . . The doctor terminals 300A, 300B, 300C, ... are installed in, for example, a first hospital HA, a second hospital HB, a third hospital HC, . . . , respectively. Further, the medical network system of the second embodiment includes an information processing device 400 provided in a service center S. Hereinafter, the medical network system of the second embodiment will be described with a focus on differences from the first embodiment.

As shown in FIG. 7, the external terminal 100 and the automated driving vehicle 200 in the medical network system of the second embodiment both have the same configuration as that of the first embodiment. Further, the plurality of doctor terminals 300A, 300B, 300C, . . . have the same configuration as the doctor terminal 300 of the first embodiment.

The information processing device 400 is connected to the network NW. The information processing device 400 includes, for example, a communication device, a calculation device, and an image display device (not shown). The information processing device 400 can receive transmission information including treatment information that is transmitted by the external terminal 100 via the network NW, using the communication device. Further, the information processing device 400 can display the received treatment information on the image display device. Further, the information processing device 400 performs a hospital guidance process on the basis of the received treatment information. In the hospital guidance process, a medical institution that is a destination candidate of the automated driving vehicle 200 is determined on the basis of a traveling position of the automated driving vehicle 200, and identification information or a location of the determined medical institution is transmitted to the communication device 220 of the automated driving vehicle 200. The hospital guidance process will be described below.

Next, processing in the medical network system of the second embodiment will be described. The processing in the medical network system of the second embodiment includes biometric information processing that is executed by the biometric information processor 242, external terminal processing that is executed by the external terminal 100, and the hospital guidance process that is executed by the information processing device 400. The biometric information processing, the external terminal processing, and the hospital guidance process are performed, for example, in a state in which an occupant gets on the automated driving vehicle 200 and the automated driving vehicle 200 is traveling toward a set destination. Hereinafter, the biometric information processing, the external terminal processing, and the hospital guidance process will be described in detail.

Figure 8:
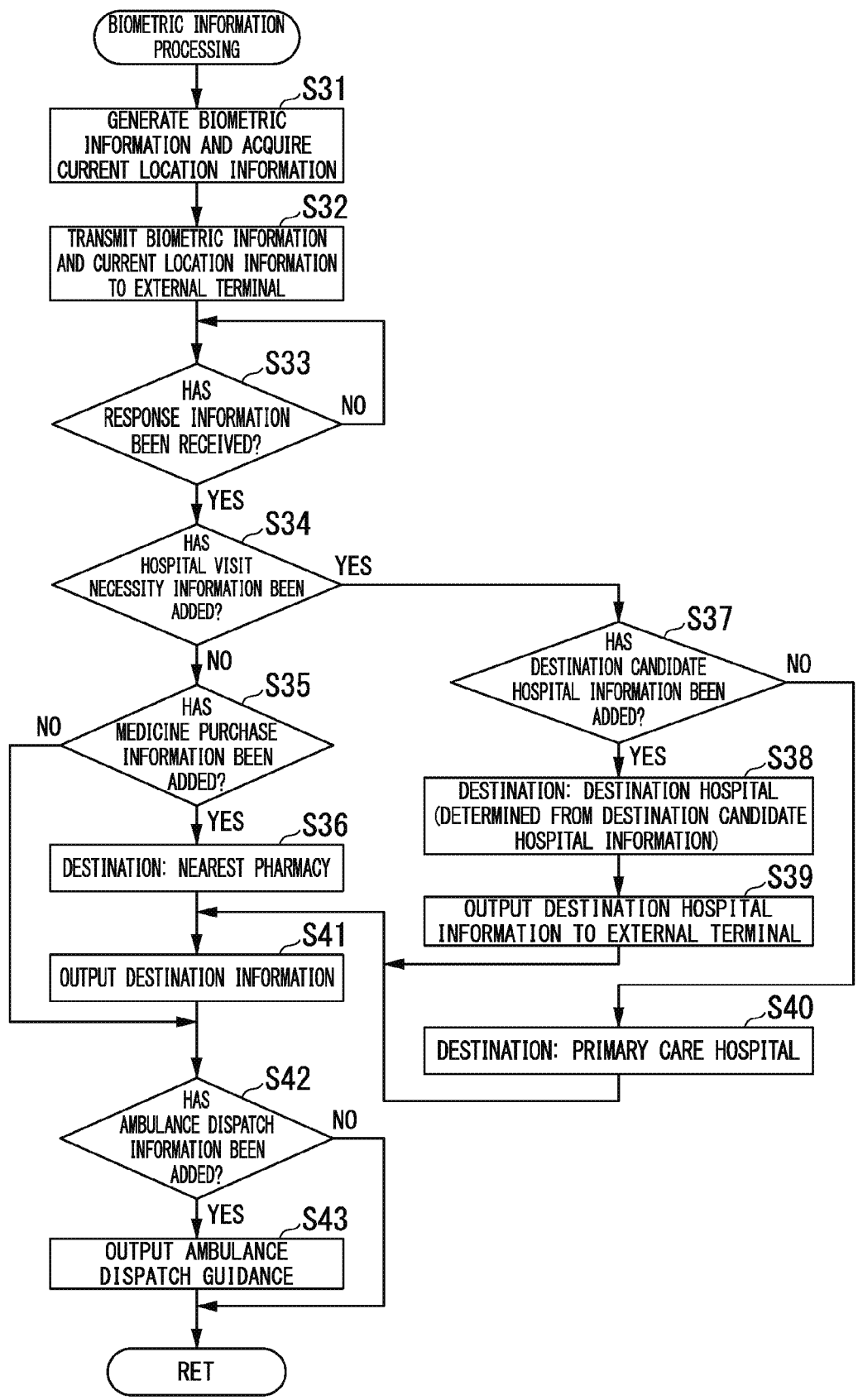
FIG. 8 is a flowchart showing a procedure of biometric information processing according to the second embodiment.

FIG. 8 is a flowchart showing an example of a procedure of biometric information processing. First, the biometric information processor 242 causes the biometric information acquirer 240 to acquire the biometric information of the user (step S31) and output the acquired biometric information to the biometric information processor 242, similar to step S11 of the first embodiment. Further, the biometric information processor 242 acquires current location information based on a current position of the automated driving vehicle 200 from the navigation device 230 (step S31).

Then, the biometric information processor 242 transmits the biometric information output by the biometric information acquirer 240 and the current location information acquired from the navigation device 230 to the controller 130 of the external terminal 100 via the communication device 220 (step S32). Subsequently, the biometric information processor 242 determines whether or not the biometric information processor 242 has received response information transmitted by the information processing device 400 of the service center S (step S33). As a result, when the biometric information processor 242 has determined that the biometric information processor 242 has not received the response information, the biometric information processor 242 repeats the process of step S33 until the biometric information processor 242 receives the response information. In a case in which the biometric information processor 242 does not receive the response information even when a predetermined waiting time such as 15 minutes has elapsed, the biometric information processor 242 may determine timeout as it is and end the biometric information processing.

The external terminal 100 performs processing based on the biometric information transmitted by the biometric information processor 242 of the automated driving vehicle 200, and transmits treatment information as a result of the processing to the information processing device 400 of the service center S. Further, the information processing device 400 generates response information on the basis of the treatment information transmitted by the external terminal 100 and transmits the response information to the biometric information processor 242. Therefore, the external terminal processing that is executed by the controller 130 in the external terminal 100 and the hospital guidance process that is executed by the information processing device 400 will be described prior to continuing the description of the biometric information processing in the biometric information processor 242.

Figure 9:
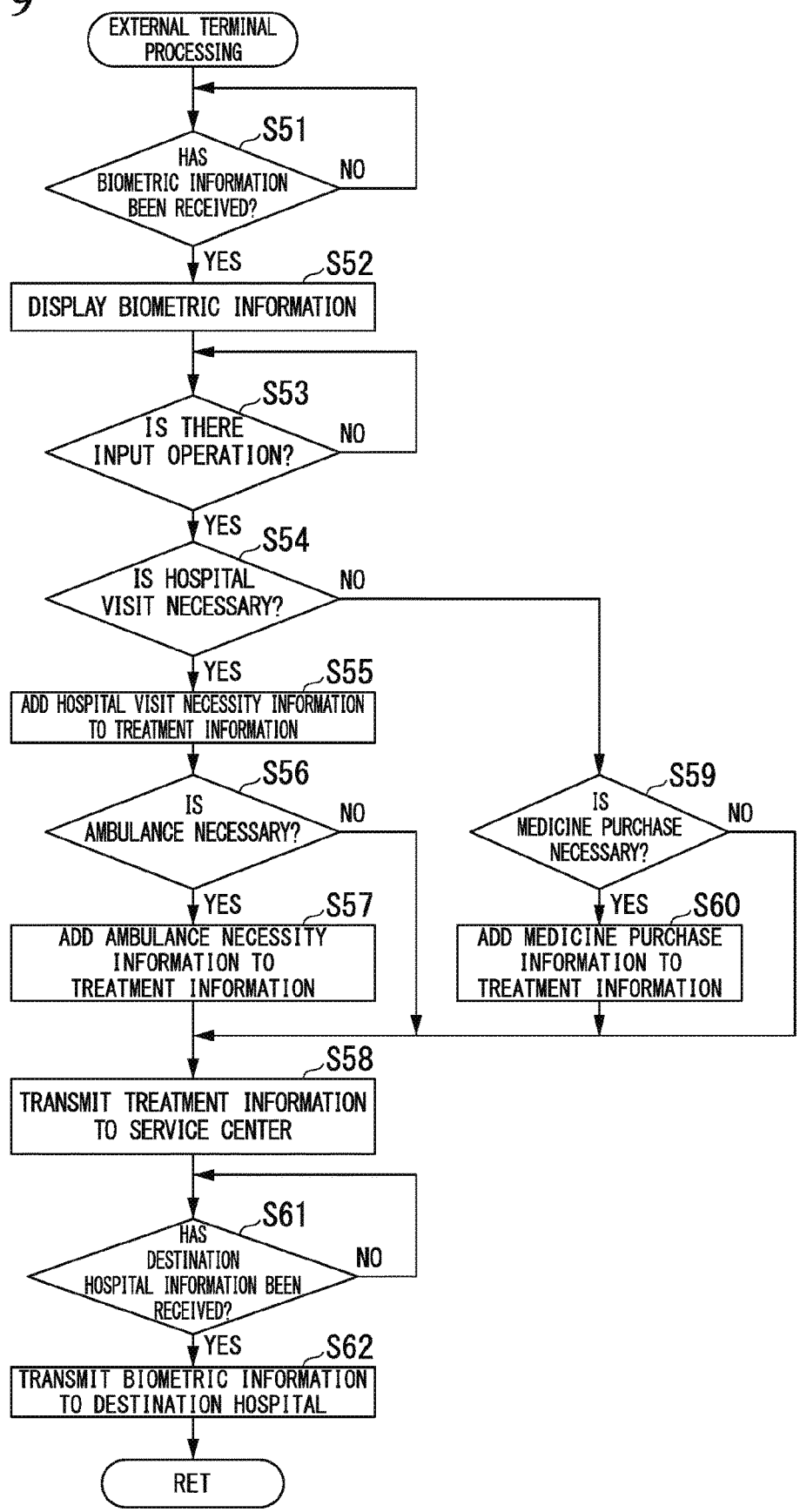
FIG. 9 is a flowchart showing a procedure of external terminal processing according to the second embodiment.

FIG. 9 is a flowchart showing an example of a procedure of the external terminal processing. First, the controller 130 in the external terminal 100 determines whether the controller 130 has received the biometric information (step S51). When the controller 130 has determined that the controller 130 has not received the biometric information, the controller 130 repeats the process of step S51. When the controller 130 has determined that the controller 130 has received the biometric information, the controller 130 displays the biometric information on the touch panel 110 (step S52) and determines whether or not there has been an input operation (step S53). As a result, when the controller 130 has determined that there has been no input operation, the controller 130 repeats the process of step S53. Thus far, the same processes as in steps S21 to S23 in the first embodiment are executed.

Further, when the controller 130 has determined in step S53 that there has been the input operation, the controller 130 determines whether or not a fact that the visit to the hospital is necessary has been input (step S54). Here, the remote diagnostician D carrying the external terminal determines whether or not a visit to any hospital, which is not a specific hospital, is necessary or whether or not a disease has a high urgency level in which, for example, there is a possibility of hospitalization, and inputs a determination result. Further, the remote diagnostician D determines whether or not an ambulance, which is a medical vehicle, is necessary, and inputs a determination result. Further, when the remote diagnostician D has determined that the visit to the hospital is not necessary and performing the administration of medicine suffices, the remote diagnostician D inputs the fact that the administration of medicine suffices and a type of medicine suitable for the administration of the medicine. In this case, as will be described below, the navigation device (an example of a proposer) 230 sets a facility outside the medical institution nearest to the automated driving vehicle 200, such as a pharmacy, as a destination, and proposes stopping by the pharmacy and purchasing medicines to the user through the HMI 232.

When the controller 130 has determined in step S54 that the visit is necessary, the controller 130 adds the hospital visit necessity information to the treatment information (step S55). An urgency level of disease is also added to the hospital visit necessity information. Subsequently, the controller 130 determines whether an ambulance is necessary (step S56). As a result, when the controller 130 has determined that the ambulance is necessary, the controller 130 adds ambulance necessity information indicating that an ambulance is necessary, to the treatment information (step S57). When the controller 130 has determined that the ambulance is not necessary, the controller 130 proceeds to step S58 without adding the ambulance necessity information.

Thereafter, the controller 130 transmits the treatment information to the information processing device 400 of the service center S (step S58). Here, the controller 130 adds the current location information transmitted by the biometric information processor 242 to the treatment information that is transmitted to the information processing device 400 of the service center S. Further, when the controller 130 has determined in step S54 that the visit to the hospital is not necessary, the controller 130 determines whether or not the visit to the hospital is not necessary and the administration of medicine suffices (step S59).

Accordingly, when the controller 130 has determined that the administration of medicine suffices, the controller 130 adds medicine purchase information according to a type of medicine to be administrated to the treatment information (step S60). Further, when the controller 130 has determined that the administration of the medicine is not necessary, the controller 130 proceeds to step S58 without adding the medicine purchase information or the like to the treatment information. Thereafter, the controller 130 adds the current location information to the treatment information and transmits the resultant treatment information to the information processing device 400 of the service center S (step S58).

Subsequently, the controller 130 determines whether or not the controller 130 has received destination hospital information that is transmitted by the biometric information processor 242 (step S61). The destination hospital information is determined by the biometric information processor 242 and transmitted to the controller 130. When the controller 130 has determined that the controller 130 has not received the destination hospital information transmitted by the biometric information processor 242, the controller 130 repeats a process of step S61. The controller 130 may determine timeout as it is and end the external terminal processing when the controller 130 does not receive the destination hospital information even when a predetermined waiting time has elapsed.

Further, when the controller 130 has determined that the controller 130 has received the destination hospital information that is transmitted by the biometric information processor 242, the controller 130 transmits the biometric information received in step S51 to the doctor terminal of a destination hospital (step S62). For example, when a first destination hospital is the first hospital HA, the controller 130 transmits the biometric information to the doctor terminal 300A. Thus, the controller 130 ends the external terminal processing.

Figure 10:
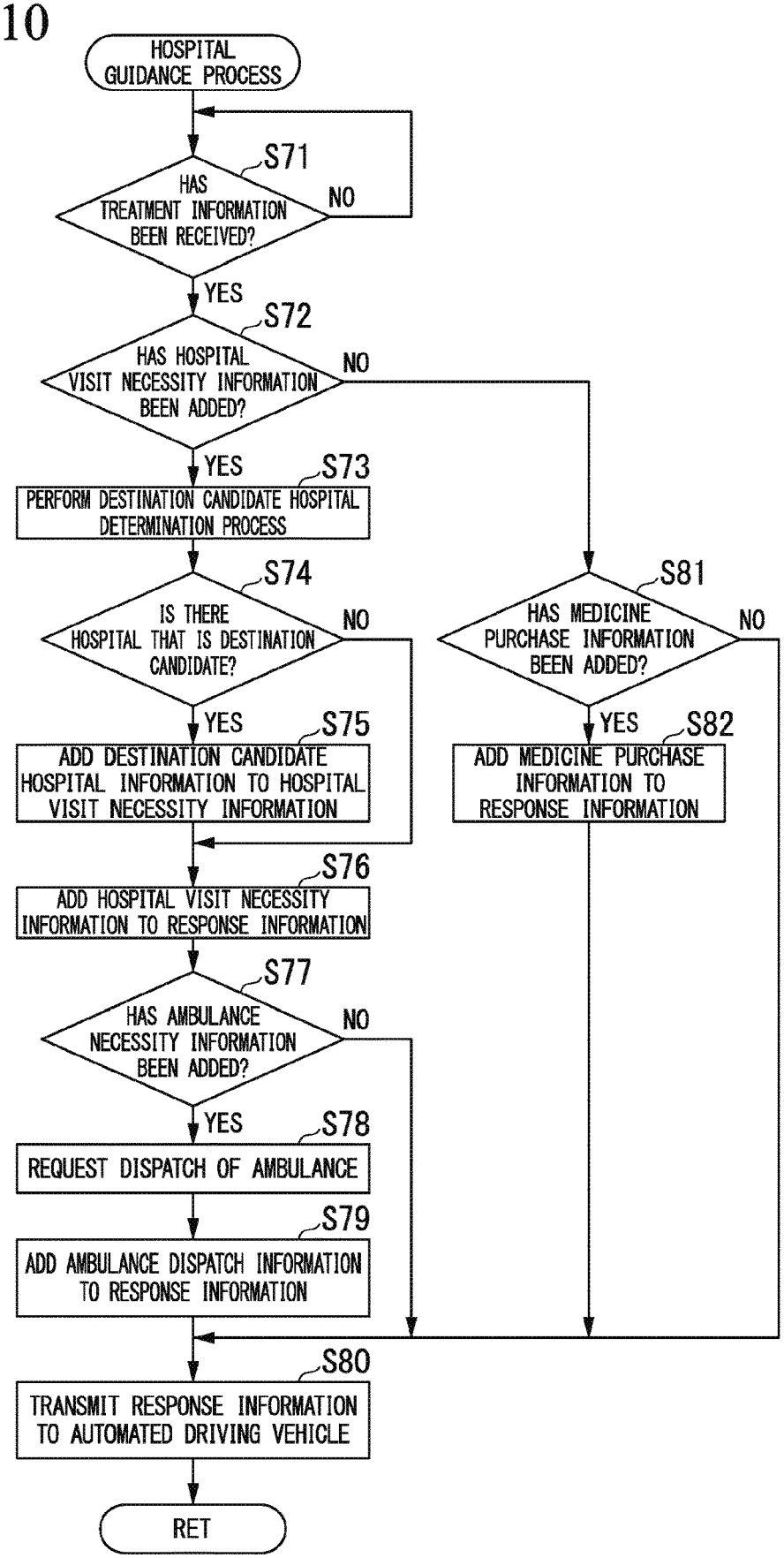
FIG. 10 is a flowchart showing a procedure of a hospital guidance process according to the second embodiment.

Next, the hospital guidance process will be described. FIG. 10 is a flowchart showing an example of a procedure of the hospital guidance process. First, the information processing device 400 in the service center S determines whether or not the information processing device 400 has received the treatment information transmitted by the external terminal 100 (step S71). As a result, when the information processing device 400 has determined that the information processing device 400 has not received the treatment information, the information processing device 400 repeats the process of step S61. When the information processing device 400 has not received the treatment information even when a predetermined waiting time has elapsed, the information processing device 400 may determine timeout as it is and end the hospital guidance process.

When the information processing device 400 has determined in step S71 that the information processing device 400 has received the treatment information transmitted by the external terminal 100, the information processing device 400 determines whether or not hospital visit necessity information has been added to the treatment information (step S72). As a result, when the information processing device 400 has determined that the hospital visit necessity information has been added to the treatment information, the information processing device 400 performs a destination candidate hospital determination process (step S73).

The information processing device 400 determines a hospital that is a candidate for the destination of the automated driving vehicle 200 in the destination candidate hospital determination process. The information processing device 400 can determine a hospital that is a candidate for the destination of the automated driving vehicle 200 according to the automated driving vehicle 200, the urgency level of the disease of the user, or the like. For example, the information processing device 400 can acquire a current traveling position of the automated driving vehicle 200 on the basis of the current location information added to the treatment information transmitted by the external terminal 100, and determine, as the destination candidate, a hospital within a radius of 10 km from the automated driving vehicle 200 of which the current traveling position has been acquired as geographical conditions. Further, the information processing device 400 may determine a hospital that is a destination candidate under temporal conditions such as a hospital that the automated driving vehicle 200 can reach, for example, in 20 minutes, in addition to the geographical conditions. Further, the information processing device 400 may also consider the urgency level of the disease to be added to the hospital visit necessity information when the information processing device 400 determines the hospital that is a candidate for the destination. For example, the information processing device 400 may determine a hospital having a hospitalization facility when a disease with a high urgency level in which hospitalization is likely to be necessary is assumed for the user, and determine a small hospital when a disease with a low urgency level is assumed for the user.

As a result of performing the destination candidate hospital determination process, the information processing device 400 determines whether or not there has been a hospital that is a destination candidate (step S74). As a result, when the information processing device 400 has determined that there has been the hospital that is a destination candidate, the information processing device 400 adds destination candidate hospital information to the hospital visit necessity information (step S75). As shown in FIG. 11, the destination candidate hospital information includes information such as an address of the hospital that is the destination candidate, a medical subject, and a non-consultation date. When the information processing device 400 has determined that there are no hospitals that are destination candidates, the information processing device 400 proceeds to step S76 as it is without adding the destination candidate hospital information.

Then, the information processing device 400 adds the hospital visit necessity information to the response information (step S76). Subsequently, the information processing device 400 determines whether or not the ambulance necessity information has been added to the treatment information (step S77). As a result, when the information processing device 400 has determined that the ambulance necessity information has been added to the treatment information, the information processing device 400 makes a request for dispatch of an ambulance AM shown in FIG. 7 (step S78). When the information processing device 400 makes a request for dispatch of the ambulance AM, the information processing device 400 transmits request information for moving the ambulance AM to a predetermined position on a route of the automated driving vehicle 200, for example.

Thereafter, the information processing device 400 adds ambulance dispatch information to the response information (step S79). Thereafter, the information processing device 400 transmits the response information to the biometric information processor 242 of the automated driving vehicle 200 (step S80) and ends the hospital guidance process. Further, when the information processing device 400 has determined in step S77 that the ambulance necessity information has not been added to the treatment information, the information processing device 400 proceeds to step S80 as it is. The information processing device 400 transmits the response information to the biometric information processor 242 of the automated driving vehicle 200 (step S80) and ends the hospital guidance process.

Further, when the information processing device 400 has determined in step S72 that the hospital visit necessity information has not been added to the treatment information, the information processing device 400 determines whether or not the medicine purchase information has been added to the treatment information (step S81). As a result, when the information processing device 400 has determined that the medicine purchase information has been added, the information processing device 400 adds the medicine purchase information to the response information (step S82) and proceeds to step S80. When the information processing device 400 has determined that the medicine purchase information has not been added, the information processing device 400 proceeds to step S80 without adding the medicine purchase information to the response information. The information processing device 400 transmits the response information to the biometric information processor 242 of the automated driving vehicle 200 (step S80) and ends the hospital guidance process.

Return to the biometric information processing shown in FIG. 8. When the biometric information processor 242 has determined in step S33 that the biometric information processor 242 has received the response information, the biometric information processor 242 determines whether or not the hospital visit necessity information has been added to the response information (step S34). As a result, when the biometric information processor 242 has determined that the hospital visit necessity information has not been added, the biometric information processor 242 determines whether or not the medicine purchase information has been added to the response information (step S35). Here, when the biometric information processor 242 has determined that the medicine purchase information has not been added to the response information, the biometric information processor 242 proceeds to step S42 as it is. Further, when the medicine purchase information has been added to the response information, the biometric information processor 242 sets a pharmacy nearest to the current location of the automated driving vehicle 200 as a destination (step S36). Further, the biometric information processor 242 outputs pharmacy information according to the medicine purchase information to the navigation device 230 when the biometric information processor 242 has set the nearest pharmacy as the destination. The navigation device 230 proposes, to the user, that the user stops by the pharmacy nearest to the automated driving vehicle 200 based on the pharmacy information output by the biometric information processor 242 and purchases medicines, through an image display or audio using the HMI 232, for example.

Figure 12:
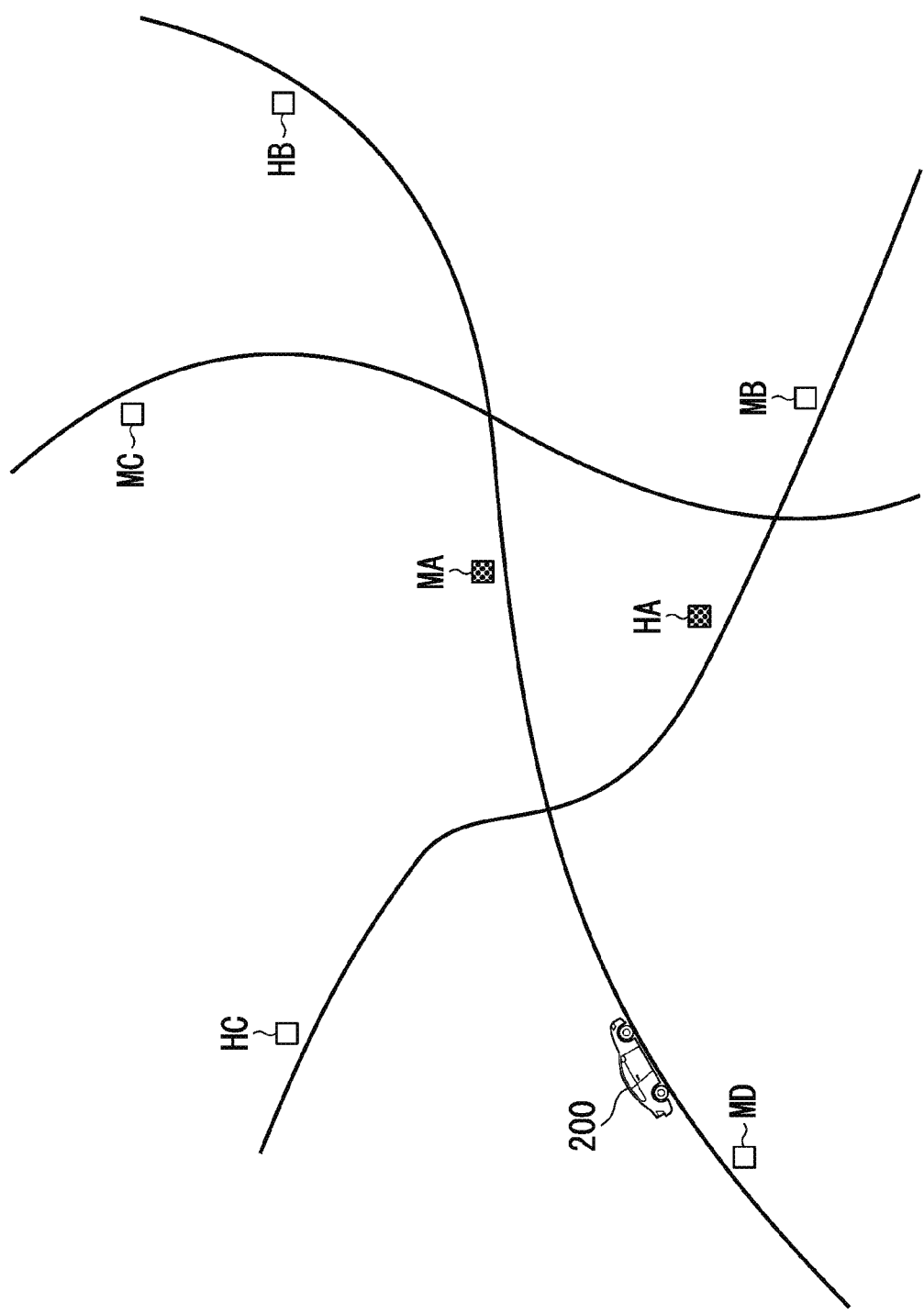
FIG. 12 is an illustrative diagram showing a map on which an automated driving vehicle can travel.

For example, when there are four first to fourth pharmacies MA to MD around the automated driving vehicle 200 as shown in FIG. 12, the biometric information processor 242 may set the fourth pharmacy MD nearest to the automated driving vehicle 200 as the destination. Further, when traveling on a road on which the automated driving vehicle 200 is traveling is restricted due to U-turn prohibition or the like, the biometric information processor 242 sets, as the destination, the first pharmacy MA that is not nearest to the automated driving vehicle 200, but to which a traveling distance is shortest.

When the biometric information processor 242 has determined in step S34 that the hospital visit necessity information has been added to the response information, the biometric information processor 242 determines whether or not the destination candidate hospital information has been added to the hospital visit necessity information (step S37). As a result, when the biometric information processor 242 has determined that the destination candidate hospital information has been added to the hospital visit necessity information, the biometric information processor 242 determines the destination hospital that is the destination (step S38). When the biometric information processor 242 determines the destination hospital, the biometric information processor 242 determines the hospital nearest to the current location of the automated driving vehicle 200 as the destination hospital from hospitals included in the destination candidate hospital information.

After the biometric information processor 242 determines the destination hospital, the biometric information processor 242 outputs the destination hospital information on the determined destination hospital to the controller 130 of the external terminal 100 (step S39). The controller 130 of the external terminal 100 executes steps S61 and S62 shown in FIG. 9 and transmits the biometric information to the destination hospital.

When the biometric information processor 242 has determined in step S37 that the destination candidate hospital information has not been added to the hospital visit necessity information, the biometric information processor 242 sets a preset primary care hospital of the occupant as the destination (step S40). When the primary care hospital of the occupant is not set, a hospital nearest to the current location of the automated driving vehicle 200 may be set as the destination. In the example shown in FIG. 12, the first hospital HA among the four hospitals including the first to fourth hospitals HA to HD may be set as the destination.

After the biometric information processor 242 sets the destination in step S36 or step S40 or sets the destination in step S38 and outputs the destination hospital information to the external terminal 100 in step S39, the biometric information processor 242 outputs the destination information to the navigation device 230 (step S41). Subsequently, the biometric information processor 242 determines whether or not the ambulance dispatch information has been added to the response information (step S42). As a result, when the biometric information processor 242 has determined that the ambulance dispatch information has been added to the response information, the biometric information processor 242 outputs an ambulance dispatch guidance (step S43). The biometric information processor 242, for example, notifies the occupant that the ambulance is called, through a sound output or image display using the HMI 232 of the navigation device 230. Thus, the biometric information processor 242 ends the biometric information processing. When the biometric information processor 242 has determined in step S42 that the ambulance dispatch information has not been added to the response information, the biometric information processor 242 ends the biometric information processing as it is.

The medical network system of the second embodiment has the same operational effects as the medical network system of the first embodiment. Further, in the medical network system according to the second embodiment, hospitals that are candidates for the destination are transmitted to the communication device 220 of the automated driving vehicle 200 on the basis of the traveling position of the automated driving vehicle 200, and the destination is determined from the hospitals that are candidates for the destination. Therefore, since a hospital that is the destination can be determined on the basis of information input by a specialist such as the remote diagnostician D, an appropriate hospital can be set when a user is directed to a destination. Further, the hospitals that are candidates for the destination are transmitted to the communication device 220 according to the urgency level of the disease.

Therefore, a more suitable hospital according to the degree of disease can be set as the destination.

Further, in the medical network system according to the second embodiment, the remote diagnostician D determines the necessity of an ambulance, and the information processing device 400 of the service center S makes an ambulance dispatch request when the ambulance is necessary. Therefore, when the user is in a disease with a high urgency level status, the ambulance can be dispatched early. Further, the ambulance is directed to a traveling route of the automated driving vehicle 200. Therefore, the ambulance can be dispatched to the automated driving vehicle 200 earlier.

Further, in the medical network system according to the second embodiment, when the remote diagnostician D determines that the visit to the hospital is not necessary and administration of a medicine that is generally sold suffices, the navigation device 230 proposes stopping by a pharmacy and purchasing medicines and the automated driving vehicle 200 sets the destination to the nearest pharmacy. Therefore, in the case of a mild disease for which the user does not have to go to a medical institution, it is possible to take a treatment to stop by a pharmacy or the like.

Third Embodiment

Figure 13:
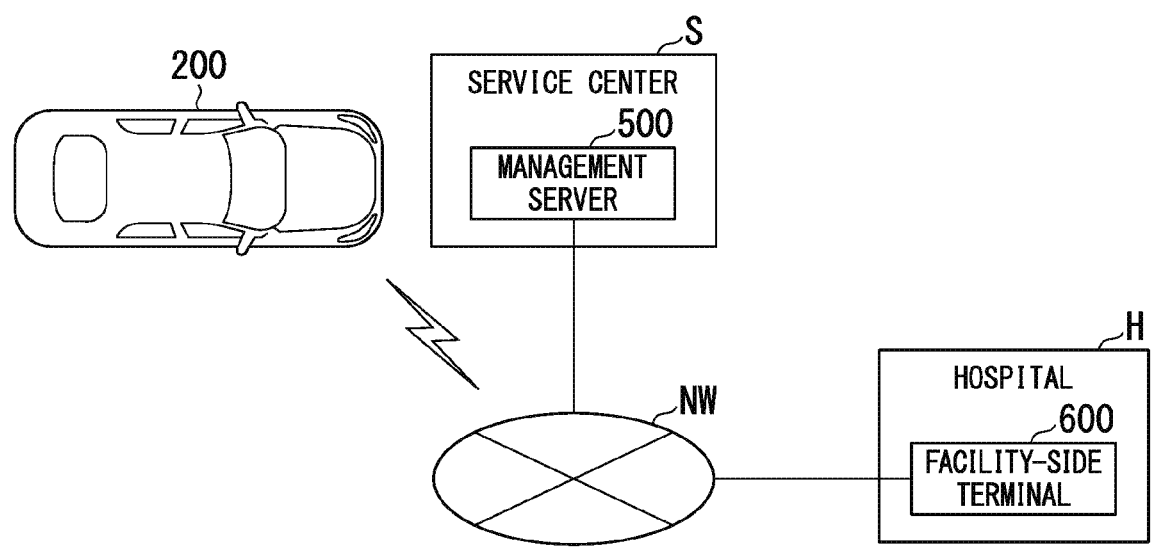
FIG. 13 is a configuration diagram of a medical network system of a third embodiment.

Next, a third embodiment will be described. In the third embodiment, a medical institution visited by the automated driving vehicle is the hospital H, as in the first embodiment. FIG. 13 is a configuration diagram of a medical network system that is a management system according to the third embodiment. As shown in FIG. 13, the medical network system according to the third embodiment includes an automated driving vehicle 200, as in the first embodiment. Further, the medical network system according to the third embodiment includes a management server 500 and a facility-side terminal 600. The management server 500 is installed in the service center S, and the facility-side terminal 600 is installed in the hospital H. Hereinafter, the medical network system according to the third embodiment will be described with a focus on differences from the first embodiment.

Figure 14:
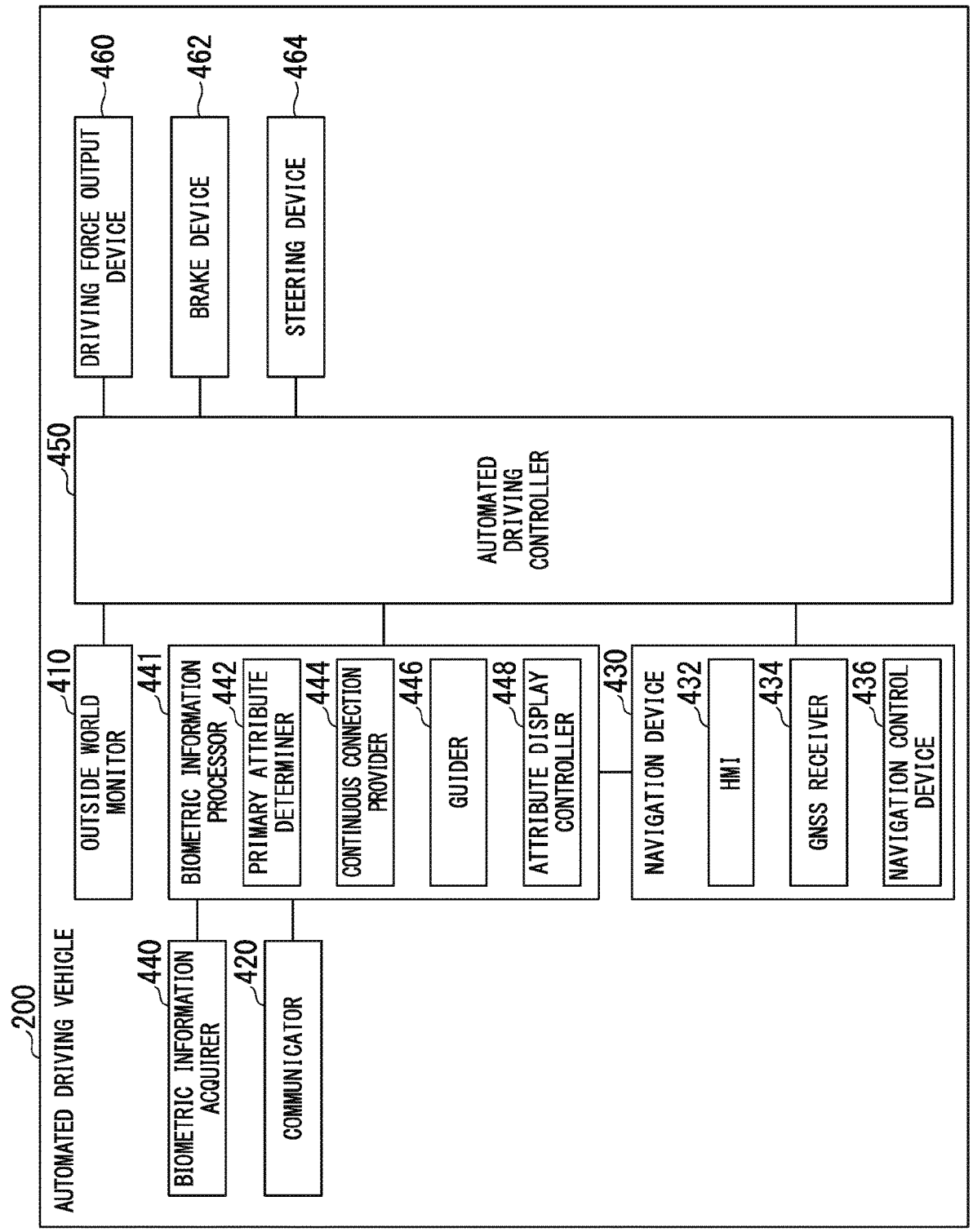
FIG. 14 is a configuration diagram of an automated driving vehicle according to the third embodiment.

FIG. 14 is a configuration diagram of the automated driving vehicle according to the third embodiment. As shown in FIG. 14, the automated driving vehicle 200 includes an outside world monitor 410, a communicator 420, a navigation device 430, a biometric information acquirer 440, a biometric information processor 441, an automated driving controller 450, a driving force output 460, a brake device 462, and a steering device 464.

Among these, the outside world monitor 410, the communicator 420, the navigation device 430, the biometric information acquirer 440, the automated driving controller 450, the driving force output 460, the brake device 462, and the steering device 464 have the same configuration as the outside world monitor 210, the communication device 220, the navigation device 230, the automated driving controller 250, the driving force output device 260, the brake device 262, and the steering device 264 in the first embodiment.

The biometric information processor 441 includes a primary attribute determiner 442, a continuous connection provider 444, a guider 446, and an attribute display controller 448. Among these, the primary attribute determiner 442 determines a primary attribute of the biometric information of the user acquired by the biometric information acquirer 440. The primary attribute is, for example, a determination result (a diagnosis result) of a determination that is the same as the diagnosis performed by the remote diagnostician D. For example, it is classified as an attribute whether or not a pulse rate or a heart rate of the user is in a range of a normal value or whether the pulse rate or the heart rate is higher or lower than the range of the normal value. The primary attribute determiner 442 transmits the classified primary attribute to the management server 500 via the communicator 420.

The continuous connection provider 444 continuously provides the biometric information acquired from the biometric information acquirer 440 as a biometric signal to the management server 500 via the communicator 420. By the continuous connection provider 444 being provided, the management server 500 can acquire the biometric information of the user in a time series and acquire a temporal change in the biometric information.

The guider 446 sets a waypoint when the automated driving vehicle 200 moves on the basis of various types of information, or performs a vehicle request determination as necessary. The guider 446 outputs the set waypoint to the navigation device 430. The navigation device 430 outputs information for traveling along the output waypoint to the automated driving controller 450. Further, when a vehicle request is made, the guider 446 transmits a vehicle request signal to the management server 500 via the communicator 420.

The attribute display controller 448 displays a display of characteristics of the biometric information determined by the primary attribute determiner 442 or various types of information transmitted from the management server 500. Further, the biometric information processor 441 includes a function that is the same as that of the biometric information acquirer 240 in the first embodiment.

Figure 15:
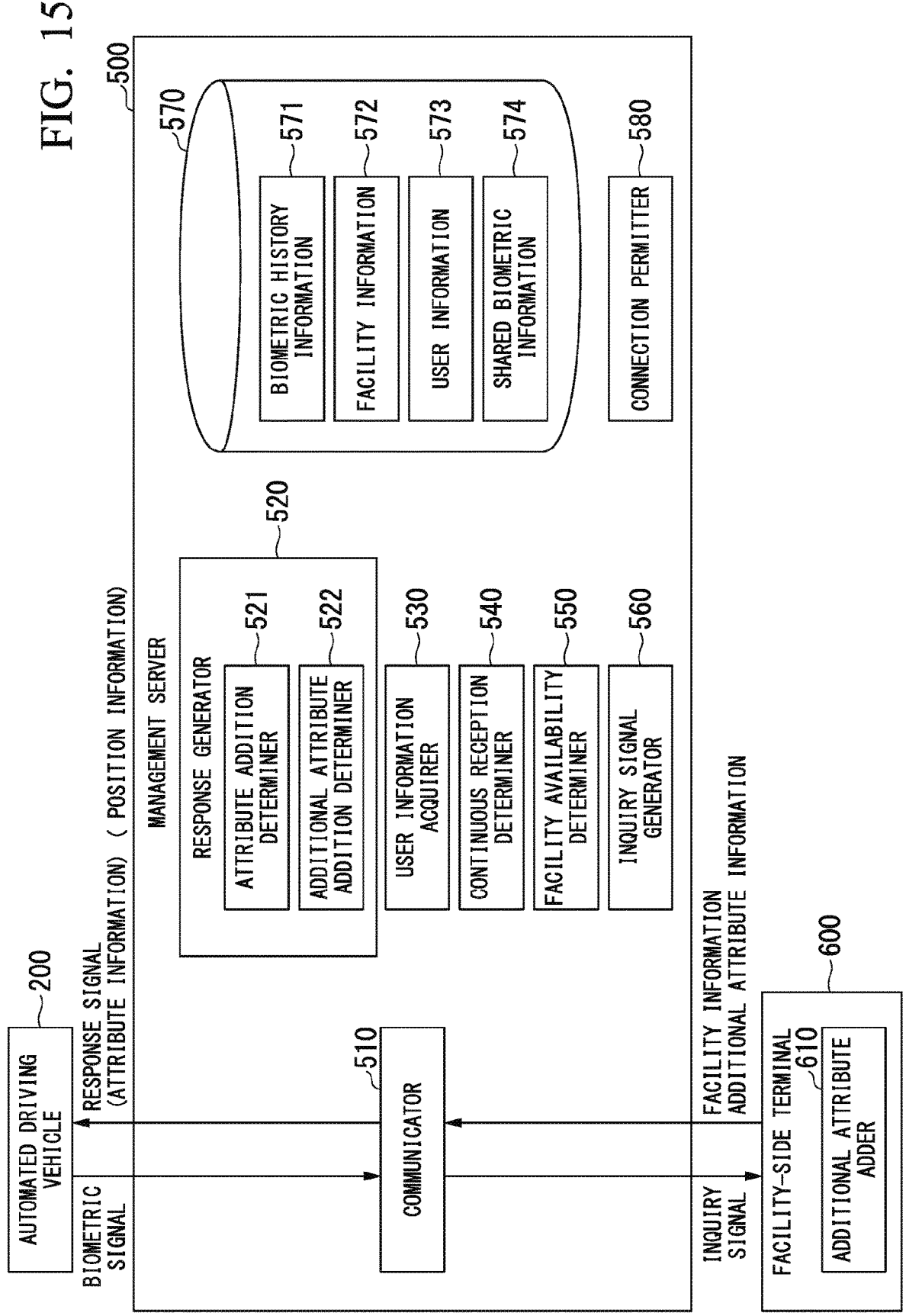
FIG. 15 is a configuration diagram of a management server of the third embodiment.

FIG. 15 is a configuration diagram of the management server of the third embodiment. As shown in FIG. 15, the management server 500 includes a communicator 510, a response generator 520, a user information acquirer 530, a continuous reception determiner 540, a facility availability determiner 550, an inquiry signal generator 560, a storage 570, and a connection permitter 580.

The response generator 520 includes an attribute addition determiner 521 and an additional attribute addition determiner 522. The storage 570 stores biometric history information 571, facility information 572, user information 573, and shared biometric information 574.

The communicator 510 transmits and receives information (signals) to and from an external device viewed from the management server 500, such as the automated driving vehicle 200 or the facility-side terminal 600. The communicator 510, for example, receives the biometric signal transmitted from the automated driving vehicle 200 and transmits a response signal to the automated driving vehicle. The response signal includes attribute information, and position information indicating a position of a facility such as a hospital. Further, the communicator 510 transmits the inquiry signal to the facility-side terminal 600 according to the available attribute information, and receives facility information and additional attribute information transmitted from the facility-side terminal 600. After the communicator 510 has transmitted the inquiry signal to the facility-side terminal 600, the communicator 510 transmits the biometric history information to the facility-side terminal 600 in response to an additional information acquisition request. When the communicator 510 transmits the biometric history information, the communicator 510 compresses and transmits the biometric history information, for example.

The attribute addition determiner 521 in the response generator 520 generates biometric information in which a secondary attribute has been added to the biometric signal transmitted from the automated driving vehicle 200 by referring to the biometric history information 571 or the like. Attribute information including secondary attribute information is added to the biometric information and transmitted as a response signal to the automated driving vehicle 200 via the communicator 510.

The additional attribute addition determiner 522 adds additional attribute information based on a result of a tertiary determination transmitted from the facility-side terminal 600 to the attribute information. The additional attribute information includes additional diagnosis necessity information that is a necessity for additional diagnosis. The additional attribute addition determiner 522 transmits the attribute information to which the additional attribute information has been added, to the automated driving vehicle 200 via the communicator 510.

The user information acquirer 530 acquires information on the user who uses the automated driving vehicle 200 by referring to the user information stored in the storage 570. The user information acquirer 530 determines the user of the automated driving vehicle 200 on the basis of the acquired user information.

The continuous reception determiner 540 determines whether or not a continuous connection for reception of the biometric signal continuously transmitted from the automated driving vehicle 200 can be made. The continuous reception determiner 540 transmits continuous connection determination authentication information to the automated driving vehicle 200 via the communicator 510 when the continuous connection can be made. Further, when the continuous connection can be made, the continuous reception determiner 540 stores the received biometric information in the storage 570 as the shared biometric information 574. The continuous reception determiner 540 serves as a signal converter. The signal converter may be provided separately from the continuous reception determiner 540.

The facility availability determiner 550 determines a facility (a medical institution) according to diagnosis content included in the attribute information by referring to the facility information stored in the storage 570. The facility availability determiner 550 determines the availability of the facility on the basis of availability information from the facility, and transmits facility information on the available facility to the automated driving vehicle 200 via the communicator 510.

The inquiry signal generator 560 generates an inquiry signal for inquiring of the facility whether or not it can be used, and transmits the inquiry signal to the facility-side terminal 600 via the communicator 510. When the inquiry signal is transmitted from the inquiry signal generator 560, the availability information is replied from the facility. The facility availability determiner 550 determines the availability of the facility on the basis of the replied availability information.

The biometric history information 571 stored in the storage 570 is a history of the biometric information that the user has acquired in the past and transmitted to the management server 500. A portion of the storage 570 in which the biometric history information 571 is stored serves as a signal holder. The facility information 572 is information on a facility in an area managed by the management server. The facility information includes position information of the facility or available attribute information. The user information 573 is, for example, information on users registered in the management server. The shared biometric information 574 is information obtained through an application programming interface (API), and is the biometric information of the user. The shared biometric information 574 is biometric information that can be shared not only with the user of the automated driving vehicle 200 but also with other external devices such as the facility-side terminal 600.

The connection permitter 580 determines whether or not a connection to a storage for the shared biometric information 574 in the management server 500 via the communicator 510 of the automated driving vehicle 200 is allowed. For example, the connection permitter 580 permits the automated driving vehicle 200 registered in the management server 500 in advance to connect to the storage for the shared biometric information 574 in the management server 500.

The facility-side terminal 600 includes an adder that adds an additional attribute. After the facility-side terminal 600 receives the inquiry signal transmitted from the management server 500, the facility-side terminal 600 determines whether or not additional diagnosis is necessary by referring to the biometric history information transmitted in response to the additional information acquisition request. The facility-side terminal 600 transmits the additional attribute information when the additional diagnosis is necessary.

Figure 16:
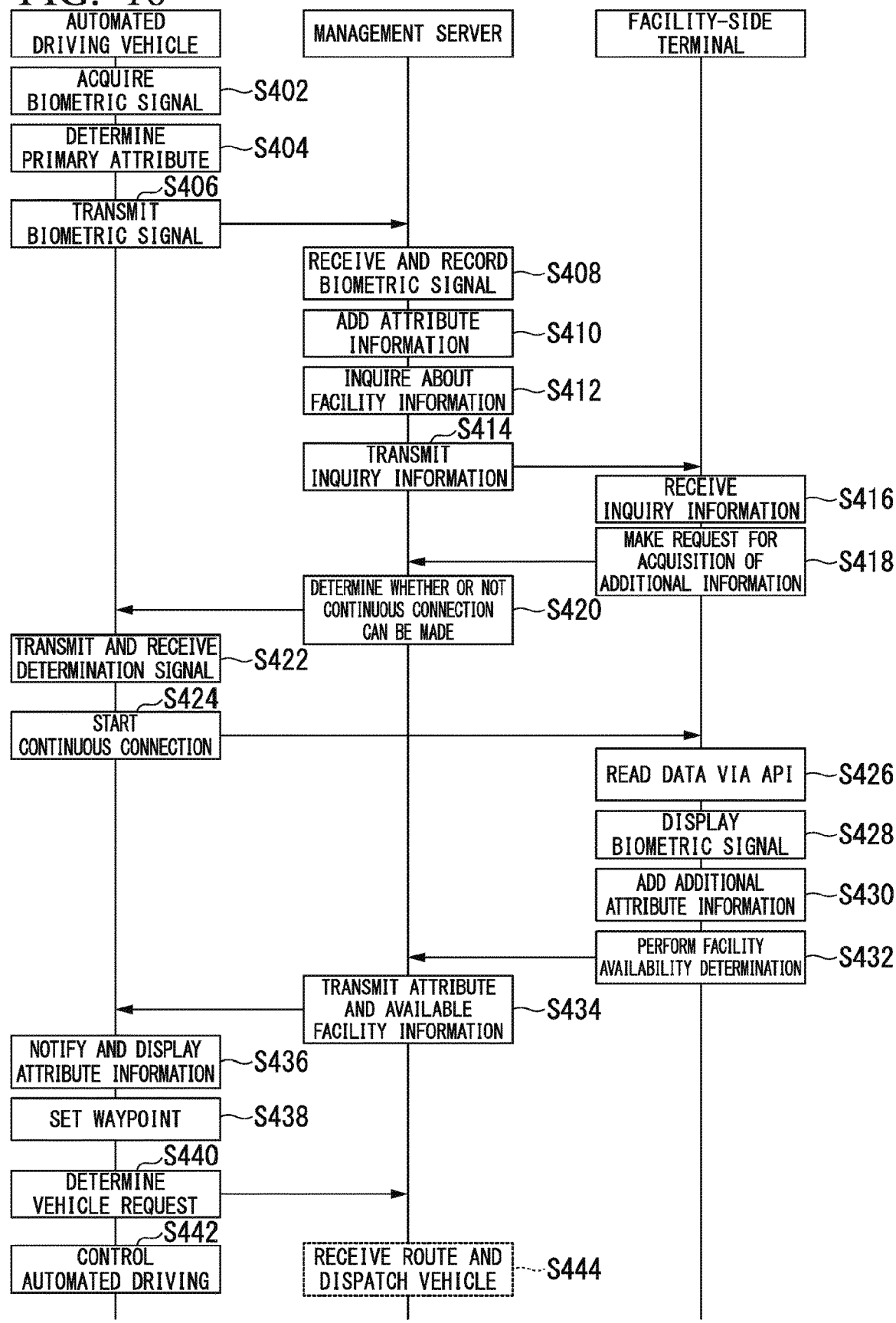
FIG. 16 is a sequence diagram showing processing that is executed by the medical network system of the third embodiment.

FIG. 16 is a sequence diagram showing processing that is executed by the medical network system according to the third embodiment. A connection between the automated driving vehicle 200 and the management server 500 shown in FIGS. 14 and 15 is started after the connection permitter 580 in the management server 500 has permitted the connection to the automated driving vehicle 200.

As shown in FIG. 16, the automated driving vehicle 200 acquires a biometric signal in the biometric information acquirer 440 (step S402), and determines the primary attribute in the primary attribute determiner 442 (step S404). Then, the automated driving vehicle 200 transmits the biometric signal subjected to the primary determination to the management server 500 (step S406).

The management server 500 receives and records the transmitted the biometric signal (step S408). Subsequently, the management server 500 adds attribute information to the biometric signal (step S410). As the attribute information here, a secondary attribute determination result based on a determination of the attribute addition determiner 521 in the management server 500 is added.

Then, the management server 500 inquires about facility information (step S412). The management server 500 inquires about a facility according to the biometric signal to which the primary attribute and the secondary attribute have been added when inquiring about the facility information. For example, the management server 500 searches for a facility according to available attribute information associating with to the primary information or the secondary information added to the biometric signal, by referring to the facility information 572 stored in the storage 570. Subsequently, the management server 500 transmits an inquiry signal to the facility that has been searched for (step S414). The inquiry signal includes the biometric signal and the attribute information.

The facility-side terminal 600 receives the transmitted inquiry signal (step S416) and makes an acquisition request for additional information (step S418). Subsequently, the connection permitter 580 of the management server 500 determines whether or not a continuous connection can be made (step S420), and transmits continuous connection determination authentication information to the automated driving vehicle 200 and the facility-side terminal 600 when the continuous connection can be made. Thus, the management server 500 performs mutual authentication with the automated driving vehicle 200 and the facility-side terminal 600.

The automated driving vehicle 200 receives the transmitted continuous connection determination authentication information (step S422) and starts the continuous connection (step S424). The automated driving vehicle 200 continuously transmits the biometric information and a primary attribute determination result to the management server 500 and the facility-side terminal 600 by starting the continuous connection (step S424).

Then, the facility-side terminal 600 reads data from the shared biometric information 574 obtained via the API (step S426) and displays the biometric signal (step S428). Subsequently, the facility-side terminal 600 determines whether or not additional diagnosis is necessary by referring to the biometric history information transmitted from the management server 500. Here, when the facility-side terminal 600 has determined that the additional diagnosis is necessary, the facility-side terminal 600 adds the additional attribute information to the biometric information (step S430). Further, the facility-side terminal 600 performs a facility availability determination (step S432) and transmits a biometric signal to which a result of the facility availability determination and the additional attribute information have been added, to the management server 500.

The management server 500 transmits a response signal including the attribute information (primary to tertiary attributes) added to the biometric signal and position information indicating a position of an available facility, to the automated driving vehicle 200 (step S434). Subsequently, the automated driving vehicle 200 notifies the user of the transmitted attribute information and displays the attribute information (step S436). Further, the automated driving vehicle 200 selects a waypoint by referring to the facility availability information and sets the waypoint (step S438). Thereafter, the automated driving vehicle 200 performs a vehicle request determination (step S440), and when a vehicle request is made, the guider 446 transmits a vehicle request signal to the management server 500 to guide an emergency vehicle (another vehicle) such as an ambulance to the route of the automated driving vehicle 200. The automated driving vehicle 200 starts automated driving control (step S442). Further, when the management server 500 has received the vehicle request signal, the management server 500 makes a request to dispatch a vehicle to a received route (step S444).

In the medical network system according to the third embodiment described above, the automated driving vehicle 200 transmits the biometric information to the management server 500 and executes automated driving according to route information based on the attribute information received from the management server 500. Therefore, the automated driving vehicle 200 can determine the necessity of a treatment to be taken by the user, such as a hospital visit treatment or a medicine administration treatment on the basis of the biometric information of the user, and move according to the biometric information of the user. Therefore, it is possible to acquire and transfer a physical status of the user quickly and sufficiently.

Although forms for implementing the present invention have been described using the embodiments, the present invention is not limited to such embodiments at all, and various modifications and substitution can be made without departing from the gist of the present invention. For example, although the remote diagnostician D and the service center S are disposed at separate positions in the second embodiment, the remote diagnostician D may stay in the service center S. In this case, a configuration in which the information processing device 400 also serves as the external terminal may be adopted.

Further, although the information processing device 400 determines the candidates for the destination of the automated driving vehicle 200 in the second embodiment, the candidates for the destination of the automated driving vehicle 200 may be determined in other aspects. For example, the remote diagnostician D may input a hospital serving as a destination candidate to the external terminal 100 so that the input destination candidate is transmitted to the biometric information processor 242. Further, the controller 130 of the external terminal 100, the information processing device 400, or the like may request a doctor to visit home or set a house of the doctor as the candidate for the destination.

Further, although the remote diagnostician D determines the necessity of the visit to the hospital in the first embodiment, the remote diagnostician D may perform, for example, the determination as to the ambulance dispatch request, and the determination as to stopping by a pharmacy without performing the visit to the hospital, as in the second embodiment. In these cases, the external terminal 100 may make the ambulance dispatch request, like the information processing device 400 in the second embodiment, to transmit request information via the communicator 120 or add the medicine purchase information and the ambulance dispatch information to response information to be transmitted to the biometric information processor 242.

Further, when the external terminal 100 receives the biometric information and transmits the response information to the biometric information processor 242 of the automated driving vehicle 200, the external terminal 100 may notify a terminal used by a person relevant to the user of user information that is information associating with the response information. Examples of the person relevant to the user may include a family member such as a parent brother, an uncle, an aunt, and a grandparent, a friend, and a colleague. When the user is a child, examples of the person relevant to the user may include a kindergarten, a nursery school, and a school that the user attends. Further, the person relevant to the use may be registered, for example, in the external terminal 100 or the like for each user in advance. Further, the user information may include information on a medical institution indicated by the hospital visit necessity information added to the response information or a pharmacy indicated by the medicine purchase information. Further, when predetermined conditions are satisfied, for example, only when the hospital visit necessity information is included, the person relevant to the user may be notified of the user information. By notifying a person relevant to the user of the user information, it is possible to early inform the person relevant to the user of the status of the user. The aspect of the notification of the user information is not particularly limited. For example, the notification may be a notification through communication via the communicator 120 or a manual notification such as a telephone call.

Further, the external terminal 100 may be provided with a notification necessity setter that sets the necessity of the notification of the user information. By the notification necessity setter being provided, the external terminal 100 can prevent an unnecessary notification from being performed. A setting operation with respect to the notification necessity setter may be performed by, for example, a user or may be performed by a person relevant to the user. Alternatively, a person other than the user or the person relevant to the user may perform the operation.

Further, although the remote diagnostician D determines the medical institution (a hospital) that is the destination of the automated driving vehicle 200 in the first embodiment, the information processing device 400 determines candidates for the destination in the second embodiment, and the biometric information processor 242 of the automated driving vehicle 200 determines the destination or the candidates for the destination, the destination of the automated driving vehicle 200 or the candidates for the destination may be determined in other aspects. For example, the medical institution (hospital) that is the destination may be determined in advance, and when the hospital visit necessity information has been added to the response information, the determined hospital may be the destination. Further, the information processing device 400 may determine the destination instead of determining the candidates for the destination. Further, when the user of the automated driving vehicle 200 rejects the destination determined by the remote diagnostician D or the like, the medical institution that is the destination may be determined again.

Further, although the external terminal 100 transmits the biometric information transmitted by the biometric information processor 242 to the doctor terminal 300 (300A, 300B, . . . ) of the hospital that is a destination in the embodiment, other aspects may be adopted. For example, the external terminal 100 may transmit the biometric information to doctor terminals of a plurality of medical institutions that can be candidates for the destination before the medical institution that is a destination is determined, or may transmit the biometric information to the doctor terminal of the medical institutions in a narrow range among the plurality of medical institutions.

Further, although the user of which the biometric information is acquired is a driver of the automated driving vehicle 200 or an occupant (a fellow occupant) other than the driver in the embodiments, the user may be one of the driver and the fellow occupant or may be both. Further, there are two modes including a mode in which biometric information of the driver is acquired and a mode in which biometric information of the fellow occupant is acquired. One of the modes may stop when the other mode is in operation.

Further, the medical network system may include a camera that images a situation of the user when the biometric information acquirer 240 acquires the biometric information, and record a biometric information acquisition situation using this camera. Further, in the second embodiment, when the service center S determines the candidates for the destination, the service center S may inquire of a plurality of medical institutions about whether the plurality of medical institutions can accept a patient, and exclude the medical institutions rejecting the acceptance from the candidates for the destination. Further, the service center S may limit a service for the medical institution according to a coping history of acceptability of each medical institution.

REFERENCE SIGNS LIST

100 External terminal
110 Touch panel
120 Communicator
130 Controller
200 Automated driving vehicle
210 Outside world monitor
220 Communication device
230 Navigation device
232 HMI
234 GNSS receiver
236 Navigation control device
240 Biometric information acquirer
242 Biometric information processor
250 Automated driving controller
260 Driving force output device
262 Brake device
264 Steering device
300 Doctor terminal
400 Information processing device
AM ambulance
D Remote diagnostician
H Hospital
NW network
S Service center

What is claim is:

1. A mobile body comprising:
a processor configured to operate as:
a biometric information acquirer configured to acquire biometric information of a user;
an automated driving controller configured to execute automated driving of the mobile body; and
a communicator configured to transmit the biometric information to an external device while the automated driving controller is executing the automated driving and receive a response signal including attribute information for the transmitted biometric information from the external device,
wherein the automated driving controller is configured to execute the automated driving according to route information formed on the basis of the biometric information acquired by the biometric information acquirer and an acquisition state of the attribute information included in the response signal, and wherein, when the biometric information acquirer is likely to be influenced by electromagnetic waves in a surrounding environment, the automated driving controller is configured to cause the mobile body to move to another place to avoid the influence of the electromagnetic waves, and then, the biometric information acquirer is configured to acquire the biometric information.

2. The mobile body according to claim 1,
wherein the attribute information includes position information according to at least one of diagnosis result information and additional diagnosis necessity information of the user, and
the automated driving controller is configured to select a waypoint from the position information included in the attribute information received by the communicator.

3. The mobile body according to claim 2, wherein the processor is further configured to operate as:
a continuous connection provider configured to continuously transmit the biometric information acquired by the biometric information acquirer to the external device through mutual authentication with the external device.

4. The mobile body according to claim 2, wherein the processor is further configured to operate as:
a guider configured to generate guidance information for guiding another mobile body to a route of the mobile body on the basis of the attribute information and the route information,
wherein the communicator is configured to transmit the guidance information to an outside.

5. The mobile body according to claim 1, wherein the automated driving controller is configured to cause the mobile body to stop or slow down while the biometric information acquirer is in operation.

6. The mobile body according to claim 1, wherein the processor is further configured to operate as:
an attribute display controller configured to control information to be displayed to the user on the basis of the attribute information.

7. The mobile body according to claim 1, wherein the processor is further configured to operate as:
a primary attribute determiner configured to determine a primary attribute regardless of the communicator.

8. A management system communicatively connectable to a mobile body comprising a biometric information acquirer configured to acquire biometric information of a user, an automated driving controller configured to execute automated driving of the mobile body, and a communicator configured to transmit the biometric information to an external device while the automated driving controller is executing the automated driving and receive a response signal including attribute information for the transmitted biometric information from the external device, the management system comprising a processor configured to operate as:

a response generator configured to add an attribute to the biometric information on the basis of the biometric information received from the communicator and generate the response signal including the attribute information;
a user information acquirer configured to acquire user information associated with the biometric information;
a transmitter configured to transmit the response signal to the communicator; and
wherein, when the biometric information acquirer is likely to be influenced by electromagnetic waves in a surrounding environment, the automated driving controller is configured to cause the mobile body to move to another place to avoid the influence of the electromagnetic waves, and then, the biometric information acquirer is configured to acquire the biometric information.

9. The management system according to claim 8, wherein the processor is further configured to operate as a facility information referrer configured to refer to facility information of an available facility on the basis of the attribute information.

10. The management system according to claim 9, comprising:
an inquiry signal transmitter configured to transmit an inquiry signal to a communication destination associated with the available facility on the basis of the attribute information; and
a facility information transmitter configured to receive an inquiry response in response to the inquiry signal from the communication destination and transmit the facility information associated with the inquiry response to the communicator.

11. The management system according to claim 8, wherein the processor is further configured to operate as:
a continuous reception determiner configured to determine whether or not the biometric information is able to be continuously received from the communicator;
a signal converter configured to convert the received biometric information and write the converted biometric information to a unit sharable with an external device in a state in which the continuous reception determiner has determined that the biometric information is able to be continuously received; and
a connection permitter configured to permit an external device to access the shareable unit.

12. The management system according to claim 10, wherein the processor is further configured to operate as:
a signal holder configured to record the biometric information from the communicator over a predetermined period; and
a history transmitter configured to transmit a biometric signal history recorded by the signal holder to the communication destination.

* * * * *